US012623091B2

(12) United States Patent (10) Patent No.: US 12,623,091 B2
Yu et al. (45) Date of Patent: May 12, 2026

(54) SKIN CARE ASSEMBLY

(71) Applicant: SHENZHEN ULIKE SMART ELECTRONICS CO., LTD., Shenzhen (CN)

(72) Inventors: Fei Yu, Shenzhen (CN); Yuping Pan, Shenzhen (CN)

(73) Assignee: SHENZHEN ULIKE SMART ELECTRONICS CO., LTD., Shenzhen (CN)

( * ) Notice: Subject to any disclaimer, the term of this patent is extended or adjusted under 35 U.S.C. 154(b) by 256 days.

(21) Appl. No.: 18/363,707

(22) Filed: Aug. 1, 2023

(65) Prior Publication Data

US 2023/0372730 A1 Nov. 23, 2023

Related U.S. Application Data

(63) Continuation of application No. PCT/CN2022/113780, filed on Aug. 19, 2022.

(30) Foreign Application Priority Data

Sep. 24, 2021 (CN) .......................... 202111124323.8

(51) Int. Cl.
$A61N 5/06$ (2006.01)
$A61N 5/00$ (2006.01)
(52) U.S. Cl.
CPC ...... *A61N 5/0616* (2013.01); *A61N 2005/007* (2013.01); *A61N 2005/065* (2013.01)

(58) Field of Classification Search
CPC ......... A61B 18/203; A61B 2018/00476; A61F 2007/0003; A61F 2007/0052;
(Continued)

(56) References Cited

U.S. PATENT DOCUMENTS

| | | | |
|---|---|---|---|
| 6,567,696 | B2 | 5/2003 | Voznesensky et al. |
| 10,835,447 | B2 | 11/2020 | Chateauvert et al. |

(Continued)

FOREIGN PATENT DOCUMENTS

| | | |
|---|---|---|
| CN | 2233733 | 8/1996 |
| CN | 101132831 A | 2/2008 |

(Continued)

OTHER PUBLICATIONS

International Search Report issued in corresponding International application No. PCT/CN2022/113780, mailed Oct. 26, 2022.
(Continued)

*Primary Examiner* — Scott Luan

(57) ABSTRACT

The present disclosure relates to the field of beauty instruments, and a skin care assembly are disclosed. The skin care assembly provided in the present disclosure includes a first cover, an electrode, and a cold compress component. The electrode is fixed on the first cover to discharge for a skin. The first cover is defined with a first opening, and the cold compress component is received in the first opening to contact and cool the skin during the electrode discharging for the skin. The electrode may provide a beauty effect to the skin by generating micro-current and radio frequency, and the cold compress component provides a suitable environment temperature for the skin, thus the beauty effect is improved.

17 Claims, 13 Drawing Sheets

(58) Field of Classification Search
CPC ...... A61F 2007/0075; A61F 2007/0078; A61F 2007/0087; A61F 7/007; A61N 1/0408; A61N 1/0472; A61N 1/328; A61N 2005/007; A61N 2005/0644; A61N 2005/065; A61N 2005/0651; A61N 2005/0662; A61N 5/0616
See application file for complete search history.

(56) References Cited

U.S. PATENT DOCUMENTS

| | | | |
|---|---|---|---|
| 2002/0107543 A1 | 8/2002 | Voznesensky et al. | |
| 2007/0135876 A1 | 6/2007 | Weber | |
| 2007/0282318 A1* | 12/2007 | Spooner | A61B 18/1206 |
| | | | 607/101 |
| 2009/0018628 A1 | 1/2009 | Burns | |
| 2014/0378887 A1 | 12/2014 | Chang et al. | |
| 2015/0045857 A1 | 2/2015 | Britva et al. | |
| 2015/0088050 A1* | 3/2015 | Chang | A61N 1/327 |
| | | | 604/20 |
| 2016/0324719 A1 | 11/2016 | Badmus et al. | |
| 2020/0387181 A1* | 12/2020 | Guo | G06K 7/10366 |
| 2021/0196968 A1 | 7/2021 | Ko | |
| 2022/0125672 A1 | 4/2022 | Wersland et al. | |

FOREIGN PATENT DOCUMENTS

| | | | |
|---|---|---|---|
| CN | 201160894 | | 12/2008 |
| CN | 104473712 | | 4/2015 |
| CN | 204733456 | U | 10/2015 |
| CN | 105050777 | | 11/2015 |
| CN | 105251119 | A | 1/2016 |
| CN | 205268825 | U | 6/2016 |
| CN | 108021181 | A | 5/2018 |
| CN | 207341852 | | 5/2018 |
| CN | 207356372 | | 5/2018 |
| CN | 108175673 | A | 6/2018 |
| CN | 207804371 | U | 9/2018 |
| CN | 207804372 | | 9/2018 |
| CN | 208142226 | | 11/2018 |
| CN | 109310460 | | 2/2019 |
| CN | 208611305 | U | 3/2019 |
| CN | 208865041 | U | 5/2019 |
| CN | 208893123 | U | 5/2019 |
| CN | 209019125 | U | 6/2019 |
| CN | 209790005 | U | 12/2019 |
| CN | 110755153 | A | 2/2020 |
| CN | 210617874 | U | 5/2020 |
| CN | 111449840 | A | 7/2020 |
| CN | 210991071 | | 7/2020 |
| CN | 111529055 | A | 8/2020 |
| CN | 211534779 | U | 9/2020 |
| CN | 211630705 | U | 10/2020 |
| CN | 112055799 | | 12/2020 |
| CN | 112370646 | A | 2/2021 |
| CN | 112484336 | | 3/2021 |
| CN | 212729957 | U | 3/2021 |
| CN | 212789460 | U | 3/2021 |
| CN | 212941026 | U | 4/2021 |
| CN | 112773503 | | 5/2021 |
| CN | 213129869 | | 5/2021 |
| CN | 213158963 | | 5/2021 |
| CN | 213190053 | | 5/2021 |
| CN | 213250259 | U | 5/2021 |
| CN | 213607350 | U | 7/2021 |
| CN | 213787756 | | 7/2021 |
| CN | 213822400 | U | 7/2021 |
| CN | 214232430 | | 9/2021 |
| CN | 215131331 | | 12/2021 |
| CN | 114681803 | A | 7/2022 |
| CN | 114796859 | A | 7/2022 |
| CN | 114796860 | A | 7/2022 |
| CN | 114796861 | | 7/2022 |
| CN | 114796862 | A | 7/2022 |
| CN | 115845263 | | 3/2023 |
| CN | 219354341 | | 7/2023 |
| CN | 219614167 | | 9/2023 |
| CN | 219614168 | | 9/2023 |
| CN | 219614734 | | 9/2023 |
| JP | H09225004 | A | 9/1997 |
| JP | 2009532079 | A | 9/2009 |
| JP | 2012152307 | A | 8/2012 |
| JP | 2017070661 | A | 4/2017 |
| JP | 2017070676 | A | 4/2017 |
| JP | 6588297 | B2 | 10/2019 |
| JP | 2021010741 | | 2/2021 |
| KR | 20030010829 | | 2/2003 |
| KR | 20090072455 | | 7/2009 |
| KR | 102123667 | B1 | 6/2020 |
| TW | M608818 | U | 3/2021 |
| WO | 2010098784 | A1 | 9/2010 |
| WO | 2012093841 | A2 | 7/2012 |
| WO | 2021174319 | A1 | 9/2021 |

OTHER PUBLICATIONS

Written Opinion of the International Search Authority in corresponding International application No. PCT/CN2022/113780, mailed Oct. 26, 2022.

* cited by examiner

01

SKIN CARE ASSEMBLY

TECHNICAL FIELD

The present disclosure relates to the technical field of beauty instruments, and in particular to a skin care assembly.

BACKGROUND

With an advancement of technology and a development of the era, people pay more and more attention to maintaining their skins. while paying attention to an effect of maintaining the skins, people also pay more and more attention to experiences during maintaining the skins. Existing beauty instruments include a contact beauty instrument adopting a radio frequency or a micro-current.

In a process of using an existing contact beauty instrument, the skin may only be heated continuously, and when a temperature of an epidermis rises to a certain level, a tingling feeling may be produced in the skin, which may bring a discomfort to a user. In addition, in a process of stimulating the skin, the epidermis and a dermis are always at high temperatures, such that the skin cannot be expanded and contracted, resulting in a general maintenance or cosmetic effect.

SUMMARY OF THE DISCLOSURE

A technical problem to be solved by the present disclosure is how to reduce a discomfort while realizing skin beauty.

In order to solve the above problem, the present disclosure provides a skin care assembly including a first cover, an electrode, and a cold compress component. The first cover defines a first opening, the electrode is fixed on the first cover and configured to discharge for skin, and the cold compress component is received in the first opening and configured to contact the skin.

The skin care assembly provided in some embodiments of the present disclosure is more using comfort and has an excellent beauty effect. The electrode provides the beauty effect to the skin by generating micro-current and radio frequency, and the cold compress component provides a suitable environment temperature for the skin, thus improving the beauty effect.

BRIEF DESCRIPTION OF THE DRAWINGS

In order to more clearly illustrate the technical solutions in the embodiments of the present disclosure, a brief description of the accompanying drawings to be configured in the description of the embodiments will be given below. It will be obvious that the accompanying drawings in the following description are only some embodiments of the present disclosure, and that other accompanying drawings may be obtained on the basis of these drawings without any creative effort for those skilled in the art.

DETAILED DESCRIPTION

In order to make the above purposes, features and advantages of the present disclosure more clear and easily understood, specific embodiments of the present disclosure will be described in detail below with reference to the accompanying drawings. It should be understood that the specific embodiments described herein are only configured to explain the present disclosure, but not limitations of the present disclosure. In addition, it should be noted that, for convenience of description, the drawings only show some but not all structures related to the present disclosure. Based on the embodiments in the present disclosure, all other embodiments obtained by those of ordinary skill in the art without creative work fall within a scope of the present disclosure.

The terms "first", "second", etc., in the present disclosure are configured to distinguish different objects and not configured to describe a specific order. In addition, the terms "include", "arranged with" "defines" and any variations thereof are intended to cover non-exclusive inclusion. For example, a process, method, system, product, or apparatus including a series of steps or units is not limited to the listed steps or regions, but in some embodiments further includes steps or units not listed, or in some embodiments further includes other steps or units inherent to the process, method, product, or apparatus.

References herein to "embodiments" mean that particular features, structures, or characteristics described in connection with some embodiments may be included in at least one embodiment of the present disclosure. The presence of the phrase at various points in the specification does not necessarily mean the same embodiment, nor is it a separate or alternative embodiment that is mutually exclusive with other embodiments. It is understood, both explicitly and implicitly, by those skilled in the art that the embodiments described herein may be combined with other embodiments.

Figure 1:
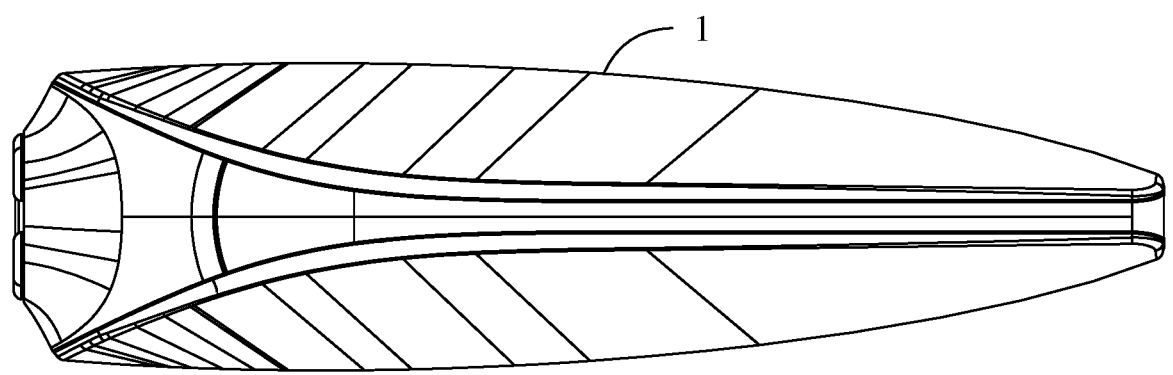
FIG. 1 is a structural schematic view of a skin care assembly according to an embodiment of the present disclosure.
Figure 2:
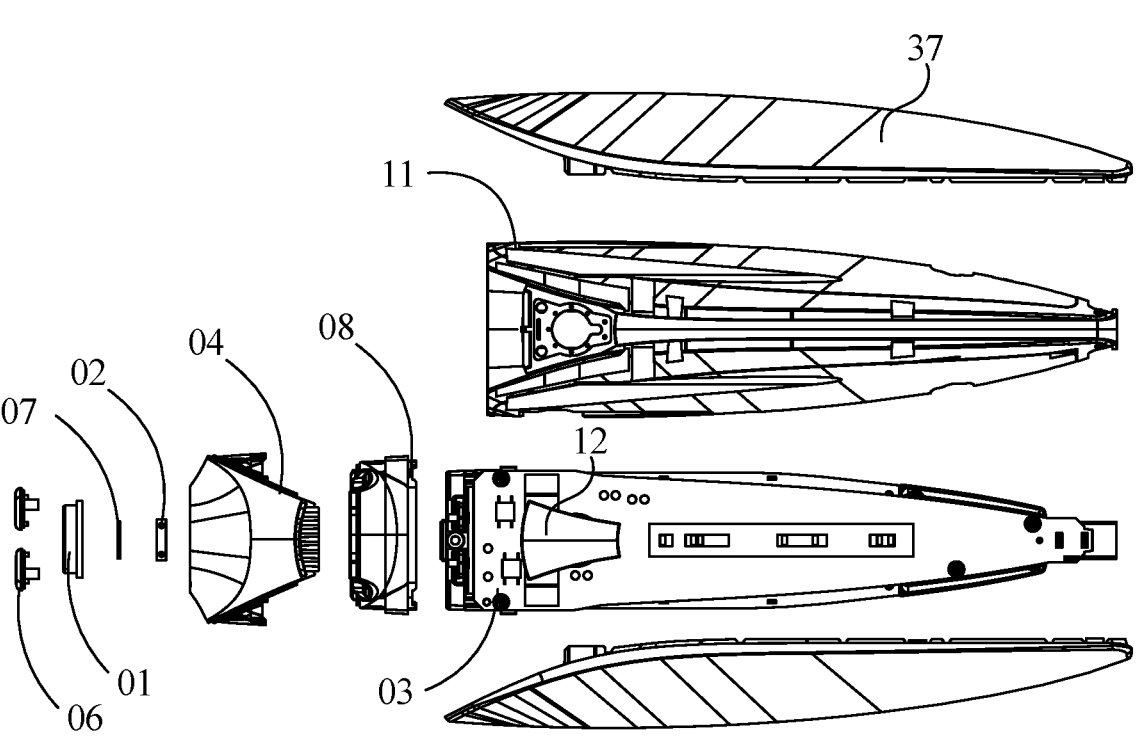
FIG. 2 is a perspective exploded schematic view of the skin care assembly in FIG. 1 in a direction.
Figure 3:
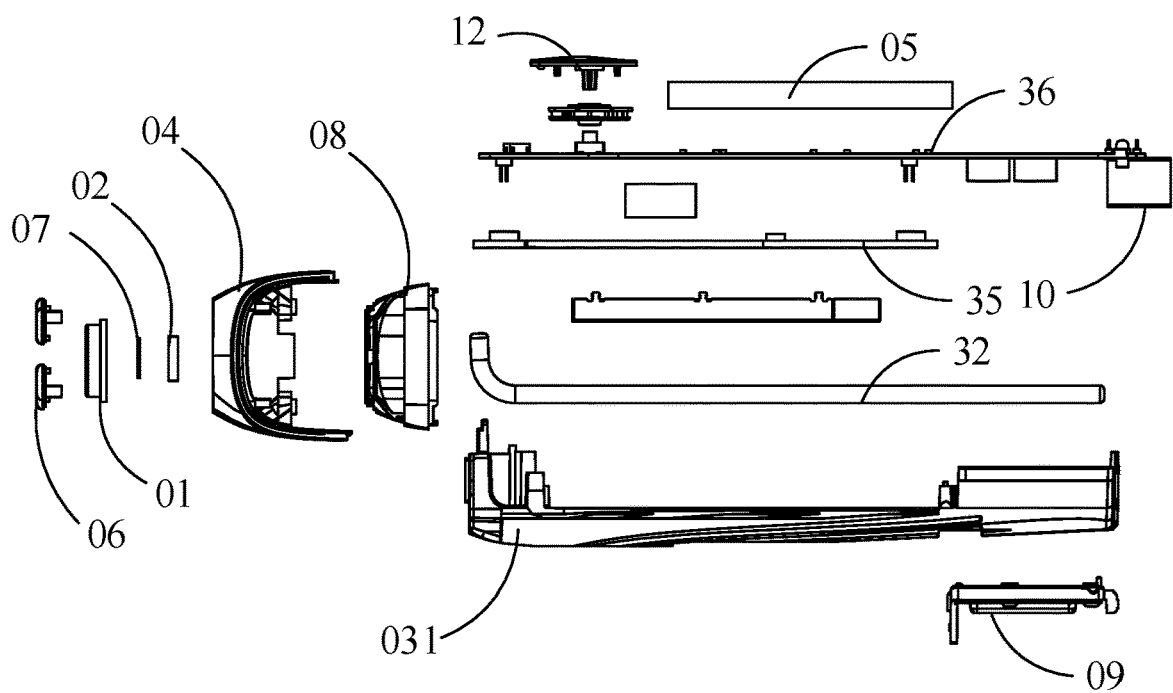
FIG. 3 is a perspective exploded schematic view of the skin care assembly in FIG. 1 in another direction.
Figure 4:
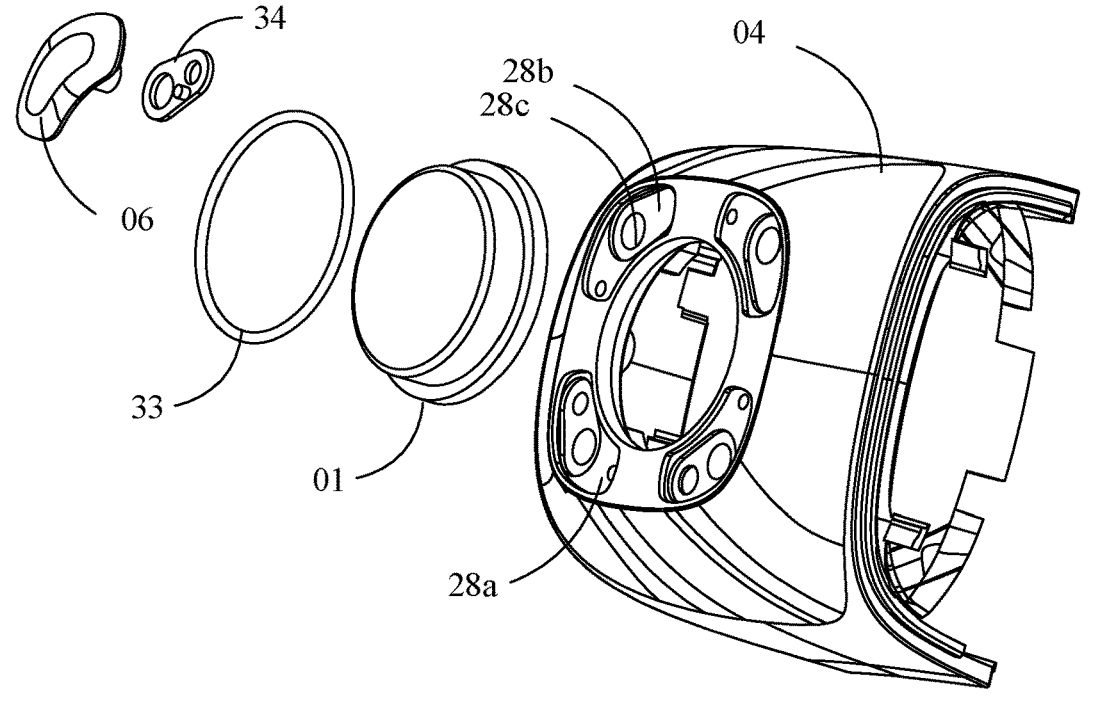
FIG. 4 is an exploded schematic view of a head portion of the skin care assembly in FIG. 1 in a direction.
Figure 5:
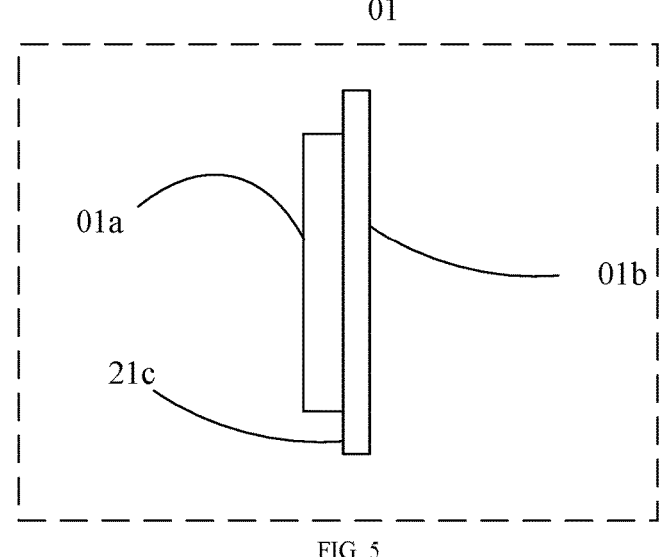
FIG. 5 is a structural schematic diagram of a cold compress component of the skin care assembly in a direction according to an embodiment of the present disclosure.

FIG. 1 is a structural schematic view of a skin care assembly according to an embodiment of the present disclosure. FIG. 2 is a perspective exploded schematic view of the skin care assembly in FIG. 1 in a direction. FIG. 3 is a perspective exploded schematic view of the skin care assembly in FIG. 1 in another direction. FIG. 4 is an exploded schematic view of a head portion of the skin care assembly in FIG. 1 in a direction. FIG. 5 is a structural schematic diagram of a cold compress component of the skin care assembly in a direction according to an embodiment of the present disclosure.

As shown in FIGS. 1 to 5, a skin care assembly 1 is provided in some embodiments of the present disclosure and includes a cold compress component 01, a refrigeration component 02, a heat sink 03, a first cover 04, and an electrode 06. The cold compress component 01 includes a contacting surface 01*a*, a conducting surface 01*b*. The contacting surface 01*a* is a portion configured to directly contact a skin. A refrigeration side of the refrigeration component 02 is thermally coupled to the conducting surface 01*b* of the cold compress component 01 to reduce a temperature of the cold compress component 01. The heat sink 03 is thermally coupled to a heat-generating side of the refrigeration component 02 to dissipate heat from the refrigeration component 02. The first cover 04 is configured to relatively fix the cold compress component 01 to the heat sink 03. The electrode 06 is fixed relative to the first cover 04. The contacting surface 01*a* and the conducting surface 01*b* of the cold compress component 01 are arranged opposite to each other, and the electrode 06 is located on a side where the contacting surface 01*a* is located. The cold compress component 01, the refrigeration component 02 and the heat sink 03 are stacked to form a sandwich structure, which may facilitate an assembly and a heat conduction of the three.

In the skin care assembly 1, the cold compress component 01 is in direct contact with the skin. The temperature of the cold compress component 01 is reduced by a refrigeration process performed by the refrigeration component 02. The heat sink 03 dissipates the heat from the refrigeration component 02. The cold compress component 01 is relatively fixed to the heat sink 03 by the first cover 04, such that the heat sink 03 may better cooperate with the refrigeration component 02 to reduce the temperature of the cold compress component 01, reducing a heat return in a short time and increasing a period of the skin care assembly 1 maintaining a temperature balance state. The electrode 06 performs a current stimulation and heating for the skin. The electrode 06 is relatively fixed to the first cover 04, such that the electrode 06 is close to the skin structurally. The electrode 06 cooperates with the cold compress component 01 to achieve a cosmetic effect such as firming the skin and shrinking pores.

When the skin care assembly 1 is in operating, the electrode 06 is discharged. For example, the electrode 06 may generate a radio frequency or a micro-current. The current passes through the skin to stimulate the skin, such that a desired cosmetic effect may be achieved. Since the skin acts as an electrical resistance, a temperature of the skin may be increased. The cold compress component 01 and the electrode 06 are fixed relative to the first cover 04. The cold compress component 10 and the electrode 06 are both in direct contact with the skin and are adjacent to each other. The current of the electrode 06 passing through the skin may cause a muscle having a contraction movement, and the cosmetic effect may be achieved. An epidermal temperature and a dermal temperature of the skin may be increased during a discharge process of the electrode 06. The temperature of the skin may be increased resulting from a heat generated by skin cells and a heat converted from an electrical energy. The cold compress component 01 is configured to reduce a heat generated by the electrode 06 stimulating an epidermis, and reduce a temperature of the epidermis of the skin. In this way, a cold compress and calm effect may be achieved, which may avoid burning the skin due to an excessive temperature, reduce a discomfort feeling in use, and improve a comfort of operating an operating member. The refrigeration component 02 performs the refrigeration process for the cold compress component 01, such that the cold compress component 01 may continuously reduce the temperature of the epidermis of the skin. A process of hot and cold being alternated may also make the skin expand and contract, enhancing a breath of the skin. In this way, collagen of a dermal layer may be better stimulated to be tightened and regenerated while the skin is protected from a damage, and the skin may be tightened, which may improve the cosmetic effect.

In some embodiments, the skin may be a facial skin. A more superficial skin may be the epidermis, and a deeper skin may be a dermis. When operating, the electrode 06 may be discharged and generate the radio frequency or the micro-current, etc., to perform a cosmetic process for the facial skin.

In some embodiments, the electrode 06 may be fixedly mounted on the first cover 04. The skin care assembly 1 may be applied in a beauty instrument.

In some embodiments, the number of electrodes 06 may be four. The electrodes 06 are arranged on a circumferential side of the cold compress component 01 and spaced from each other. A height of an upper surface of the electrode 06 close to the skin flushes with a height of the contacting surface of the cold compress component 01, that is, the electrodes 06 and the cold compress component 01 may be simultaneously in direct contact with the skin. In this way, the cosmetic effect such as firming the skin and shrinking the pores, etc., may be achieved.

In some embodiments, a material of the cold compress component 01 may be a crystal and/or a metal.

In some embodiments, the cold compress component 01 may be a material having a good thermal conductivity, such as a sapphire, a Topaz, a rock crystal, a glass, or the like, and configured to directly contact the skin and reduce the temperature of the epidermis. For example, the cold compress component 01 made of a sapphire material has the good thermal conductivity and is skin-friendly.

In some embodiments, the cold compress component 01 may be in a shape of a circle, an oval, or a polygon. The polygon may be, for example, a square, a rectangle, a pentagon, a hexagon, etc. The shape of the cold compress component 01 is not specifically limited herein.

In some embodiments, the contacting surface 01a of the cold compress component 01 may have an area between 350 mm$^2$ and 450 mm$^2$, a thickness between 2 mm and 5 mm, and a ratio of the area of the contacting surface 01a of the cold compress component 01 to the thickness of the contacting surface 01a of the cold compress component 01 is between 88:1 and 225:1.

In some embodiments, a total power when all electrodes 06 are discharged is between 5 watts and 20 watts. When the skin care assembly 1 is in operating, a temperature of the dermis of the skin is between 50° C. and 70° C. An operating power of the refrigeration component 02 is configured to have the temperature of the skin reduced to a range between 15° C. and 45° C.

In some embodiments, the electrode 06 may include an arc-shaped body and a fixing portion protruding from the arc-shaped body towards the cold compress component 01, and the fixing portion is located on a side of the arc-shaped body facing the cold compress component 01. Multiple electrodes 06 are spaced from each other, and a circle is defined by arc-shaped bodies of the multiple electrodes 06, which may exactly enclose the contacting surface 01a of the cold compress component 01 or may also partially overlaps with the contacting surface 01a.

In some embodiments, the cold compress component may include the cold compress component 01 and a cold-conducting layer 07. The cold-conducting layer 07 is arranged between the cold compress component 01 and the refrigeration component 02 and configured to conduct a heat between the cold compress component 01 and the refrigeration component 02. The cold-conducting layer 07 abuts against the cold compress component 01.

Specifically, the cold-conducting layer 07 is further arranged between the conducting surface 01b of the cold compress component 01 and the refrigeration side of the refrigeration component 02. In this case, due to an existence of the cold-conducting layer 07, the conducting surface 01b of the cold compress component may transfer to a side of the cold-conducting layer 07 facing away from the cold compress component and directly contact with the refrigeration side of the refrigeration component 02. Since the cold-conducting layer 07 has a good thermal conductivity, the refrigeration component 02 may efficiently reduce the temperature of the cold compress component 01 through the cold-conducting layer 07.

In some embodiments, the conducting surface 01b of the cold compress component is in direct surface-contact with the refrigeration side of the refrigeration component 02. With a surface-contact manner, the heat conduction may be more sufficient and a conduction effect may be maximized.

In some embodiments, since the conducting surface 01b of the cold compress component is in direct surface-contact with the refrigeration side of the refrigeration component 02, a gap is inevitable in a contact between the two. Therefore, the cold-conducting layer 07 may be made of an aluminum nitride ceramic or other materials having good thermal conductivity. The surface-contact manner may maximize a heat-transferring effect. Both the cold compress component 01 and the cold-conducting layer 07 are made of materials having good heat-transferring performances.

In some embodiments, the cold-conducting layer 07 may be filled with a thermally conductive silicone grease, such that a heat transfer may be more sufficient, a control for the temperature may be smoother, and a feeling of the skin may be more comfortable.

In some embodiments, the skin care assembly 1 may further include a second cover 08, a first mounting plate 35, a second mounting plate 36, an inner housing 11, a button 12, a charging port 10, and a thermally conductive housing 09, or the like. The sapphire in some embodiments of the present disclosure may be artificial or natural.

In some embodiments, the skin care assembly 1 may further include a lead wire and a wire groove. The lead wire is connected to and fixed on a side of the refrigeration element 02. The wire groove is defined in an inner side of the second cover 08 corresponding to the side where the lead wire is arranged of the refrigeration element 02, and defined along an edge of a limiting hole 24 (referring to FIG. 18).

In some embodiments, lead wires may include at least one lead wire. The number of wire grooves is consistent with the number of the lead wires, and the lead wires are accommodated in the wire grooves in a process of assembling the skin care assembly 1, such that the refrigeration component 02 and the heat sink 03 may be connected and fixed together.

A skin care assembly 1 is also provided in the present disclosure, as shown in FIGS. 2 and 3. The skin care assembly 1 may include the operating member, a mounting bracket 03, and a circuit board. The operating member includes a cold compress component 01 and a refrigeration component 02 located at a head portion of the skin care assembly 1, and has a contacting surface 01a configured to directly contact the skin and reduce a temperature of the skin. The mounting bracket 03 includes a first mounting position and a second mounting position. The operating member is fixed to the mounting bracket 03 through the first mounting position, and the circuit board is fixed to the mounting bracket 03 through the second mounting position. The operating member is located at the head portion of the skin care assembly 1, and the mounting bracket 03 extends from the head portion of the skin care assembly 1 to a tail of the beauty instrument. Both the operating member and the circuit board are mounted on the mounting bracket 03, such that the assembly of each component of the skin care assembly 1 may be more centralized. In this way, a convenient assembly may be achieved, and an overall structure of the skin care assembly 1 may be more compact, such that a volume of the skin care assembly 1 may be reduced.

In some embodiments, the mounting bracket 03 may also serves as a heat sink to dissipate a heat from the beauty instrument while the mounting bracket 03 is mounted with various components, namely, the mounting bracket 03 may also be a heat sink. The mounting bracket 03 is in tight contact with a component such as the operating member in the beauty instrument, which is conducive to a sufficient and uniform heat dissipation. When the beauty instrument is in operating, the mounting bracket 03 may absorb the heat in the whole beauty instrument, making the heat dissipation more efficient. The mounting bracket 03 extending to the tail of the beauty instrument allows the heat to stay for a longer time and not to backtrack in a short time, which increasing a refrigeration period of the operating member.

In some embodiments, the skin care assembly may include the thermally conductive housing 09, and the mounting bracket 03 includes a third mounting position configured to mount the thermally conductive housing 09.

In some embodiments, a side surface of the mounting bracket 03 defines a groove, and both the second mounting position and the third mounting position are arranged or defined in the groove.

In some embodiments, in the groove, the second mounting position may be located at a position having a depth different from a depth of a position where the third mounting position is located, such that the circuit board and the thermally conductive housing 09 may be stacked. The second mounting position is farther from a bottom of the groove than the third mounting position. A stacked arrangement allows various parts to be more orderly arranged on the mounting bracket 03 without interfering with each other.

In some embodiments, a ratio of a distance from the second mounting position to the bottom of the groove to a distance from the third mounting position to the bottom of the groove may be between 1.5 and 3 times.

In some embodiments, the skin care assembly includes the second mounting plate 36 and the button 12.

The button 12 is arranged on the second mounting plate 36. A side wall of the groove is arranged with a step, and the circuit board is fixed in the groove through the step. The first mounting plate 36 is fixed to the side wall of the groove, and is located on a side of the circuit board facing away from the bottom of the groove.

In some embodiments, the skin care assembly includes a first mounting plate 35. The circuit board is mounted on the first mounting plate 35, the first mounting plate 35 is mounted on the step, and the first mounting plate 35 is spaced from the bottom of the groove.

In some embodiments, the second mounting plate 36 extends to the tail of the skin care assembly, and an end of the second mounting plate 36 away from the operating member is defined with a charging port 10 configured to be connected to the circuit board.

In some embodiments, the first mounting board 35 and the second mounting board 36 themselves may also be circuit boards.

In some embodiments, a ratio of a length of the second mounting plate 36 to a length of the mounting bracket 03 is between 1.2 and 2. The charging port 10 is spaced from the mounting bracket 03 by a certain distance, and the distance is between 1 cm and 3 cm.

In some embodiments, the mounting bracket 03 defines a receiving cavity. The receiving cavity is defined on a side surface of the first mounting position and configured to accommodate a part of the lead wires in the skin care assembly.

In some embodiments, the mounting bracket 03 extends from the head portion of the skin care assembly 1 to the tail of the skin care assembly 1. The operating member cools down the skin or a surface layer of an adjacent tissue of the skin, and a depth of action of an electricity, a magnetism, or an electromagnetic emitted by the electrodes on the skin is greater than that on the surface layer. At the same moment, an area of the contacting surface 01*a* is greater than an area where the electrodes act on the skin.

In some embodiments, the skin care assembly 1 further includes the charging port 10. The charging port 10 is arranged at an ending end of the second mounting plate 36 and exposed out of the skin care assembly 1. The second mounting plate 36 may be configured to be mounted with a component or an element necessary for the skin care assembly 1 such as the circuit board, a battery, etc. The skin care assembly 1 may be used when powered on or after charged. When used after charged, the skin care assembly 1 charges for the battery by the charging port 10 being connected to an external power cord. When the skin care assembly 1 is used when powered on, the charging port 10 may generate a certain impedance due to adopting a point-contact manner inside the charging port 10, and heat may be generated when a current passes through the charging port 10. Therefore, the charging port 10 is defined at an end of a mounting plate and away from the heat sink 03, which may avoid the heat generated by the charging port 10 backtracking to the skin care assembly 1 or even the operating member. The heat generated by the charging port 10 backtracking to the skin care assembly 1 or the operation head may affect a refrigeration effect of the refrigeration component 02, thereby affecting the cosmetic effect.

In some embodiments, the skin care assembly 1 further includes an airflow driver. The airflow driver is arranged opposite to the heat sink and configured to drive airflow near the heat sink to flow so as to enhance a heat-dissipating effect.

In some embodiments, the airflow driver may be arranged on a position of the skin care assembly 1 close to the head portion. The airflow driver drives the airflow to flow from the head portion to the tail of the skin care assembly 1 and be discharged from an air outlet at the tail of the skin care assembly 1. For example, the airflow driver is a fan, and the fan is located at the head portion and blows air against the heat sink 03. The tail of the skin care assembly 1 defines the air outlet corresponding to a tail of the heat sink 03 to discharge the airflow carrying heat.

In some embodiments, the heat sink 03 extends from the head portion of the skin care assembly 1 to the tail of the skin care assembly 1. An end of the heat sink 03 located at the tail of the skin care assembly 1 is spaced from the tail by a gap, and a size of the gap is less than one third of a length of the skin care assembly 1.

The heat sink 03 includes the second cover 08 and a heat-dissipating body 031. The second cover 08 is disposed between the heat-dissipating body 031 and the first cover 04, and fixed to the heat-dissipating body 031. The first cover 04 is fixed on the second cover 08.

In some embodiments, the second cover 08 may be a light-transmitting plate 13.

In some embodiments, the second cover body 08 further defines the limiting hole 24. A position of the limiting hole 24 corresponds to a position of a first opening 50 (referring to FIG. 23) of the first cover 04. The limiting hole 24 is fluidly communicated with the first opening 50 of the first cover 04. A part of the refrigeration component 02 is arranged in the limiting hole 24, and an edge of the refrigeration component 02 is 0.5-1 mm away from an edge of the limiting hole 24.

In some embodiments, a ratio of an area of the limiting hole 24 to an area of the first opening 50 of the first cover 04 is between 0.8 and 1.2.

Figure 12:
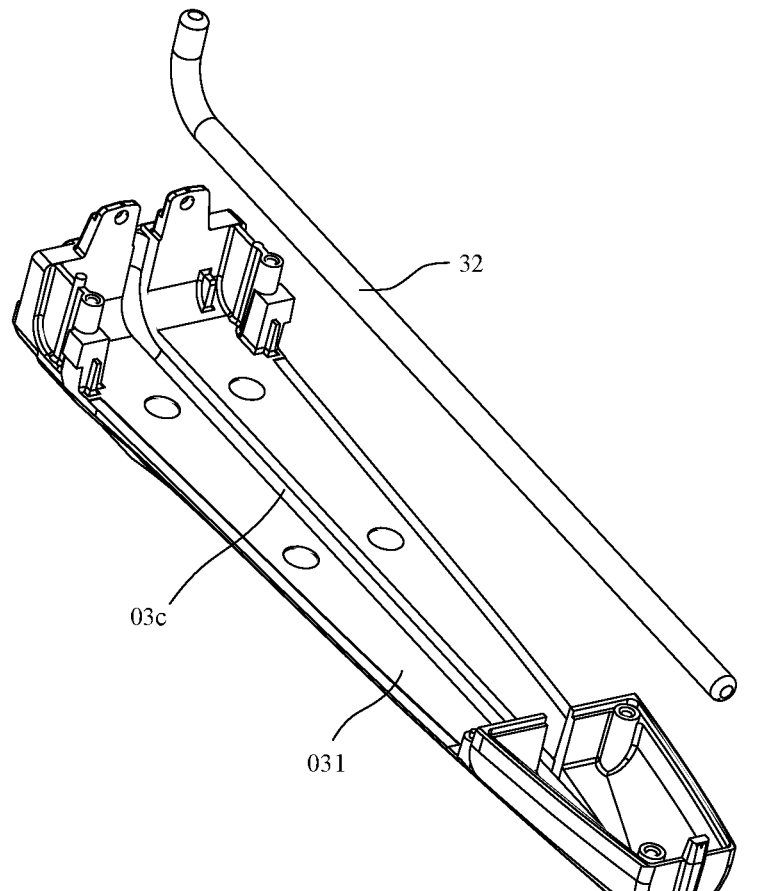
FIG. 12 is a structural schematic view of a heat-dissipating body of the skin care assembly in a direction according to an embodiment of the present application.
Figure 13:
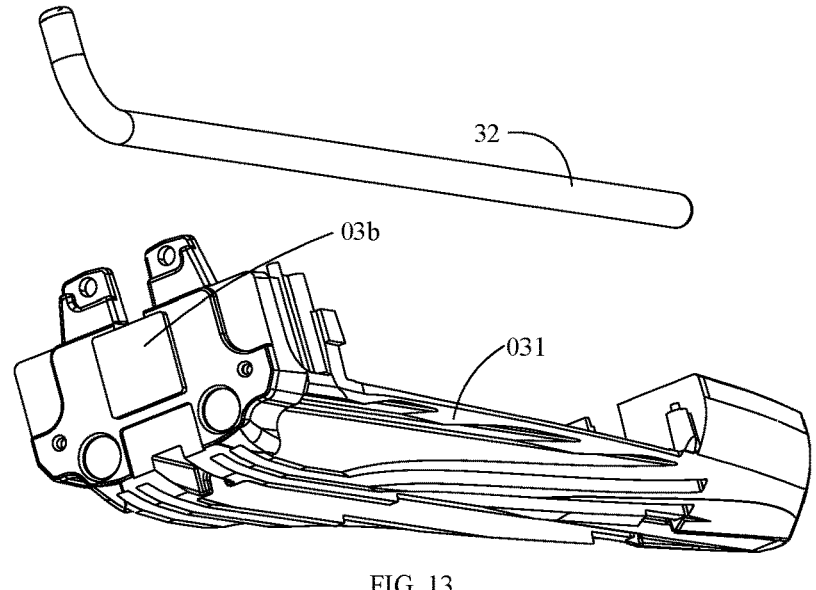
FIG. 13 is a structural schematic view of the heat-dissipating body shown in FIG. 11 in a second direction.
Figure 14:
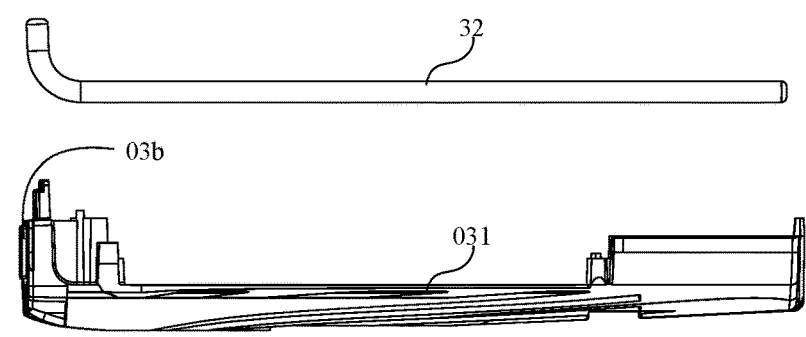
FIG. 14 is a structural schematic view of the heat-dissipating body shown in FIG. 11 in a third direction.

FIG. 12 is a structural schematic view of a heat-dissipating body of the skin care assembly in a direction according to an embodiment of the present application. FIG. 13 is a structural schematic view of the heat-dissipating body shown in FIG. 12 in a second direction. FIG. 14 is a structural schematic view of the heat-dissipating body shown in FIG. 12 in a third direction.

As shown in FIGS. 12 to 14, a skin care assembly 1 is further provided in the present disclosure and includes a heat pipe 32 and a heat-dissipating body 031. An end of the heat pipe 32 is thermally coupled to an end of the heat-dissipating body 031 close to the second cover 08, and the other end of the heat pipe 32 extends along a direction away from the refrigeration component 02 and is thermally coupled to the heat-dissipating body 031.

The heat-dissipating body 031 itself has a heat-dissipating function, and the heat pipe 32 assists the heat-dissipating body 031 to dissipate the heat, thereby improving a heat-dissipating efficiency of the heat-dissipating body 031. The end of the heat pipe 32 is thermally coupled to the end of the heat-dissipating body 031 close to the second cover 08, and the other end of the heat pipe 32 extends along the direction away from the refrigeration component 02, such that a path for transferring the heat may be long enough to avoid the heat backtracking to the head portion of the beauty instrument in a short time, and a refrigeration period of the beauty instrument may be increased.

In some embodiments, a section of the heat pipe 32 is bent to form a bent portion, and the bent portion abuts against the end of the heat-dissipating body 031 close to the second cover 08. An inside of the heat pipe 32 has a hollow and closed structure, with liquid filled inside. The heat pipe 32 is not filled up with the liquid. By arranging the bent portion of the heat pipe 32, a contacting area between the heat pipe 32 and the end of the heat-dissipating body 031 close to the second cover 08 may be increased, such that the heat pipe 32 may enhance in a targeted manner that the heat-dissipating body 031 absorbs the heat of the heat-generating side of the refrigeration component 02.

In some embodiments, the heat-dissipating body 031 defines an escape groove 03c. The heat pipe 32 is arranged along an inner wall of the escape groove 03c, at least partially embedded in the escape groove 03c, and welded to the inner wall of the escape groove 03c. An end of the heat pipe 32 away from the bent portion extends to an ending end of the heat-dissipating body 031, such that a contact between the 32 and the heat-dissipating body 031 may be more sufficient, which may improve a heat-dissipating performance of the heat sink 03.

In some embodiments, a contacting portion 03b is arranged on a side surface of the heat-dissipating body 031 close to the refrigeration component 02. A position of the contacting portion 03b corresponds to the position of the limiting hole 24. The heat-generating side of the refrigeration component 02 may be thermally coupled to the contacting portion 03b through the limiting hole 24.

In some embodiments, when the contacting portion 03b is a boss, a part of the contacting portion 03b is located in the limiting hole 24, attached to the heat-generating side of the refrigeration element 02, and fixed relative to the heat-generating side of the refrigeration element 02.

In some embodiments, the heat-dissipating body 031 is made of aluminum by means of integral molding. An end of the heat-dissipating body 031 away from the escape groove 03c has a heat-dissipating fin structure.

Figure 18:
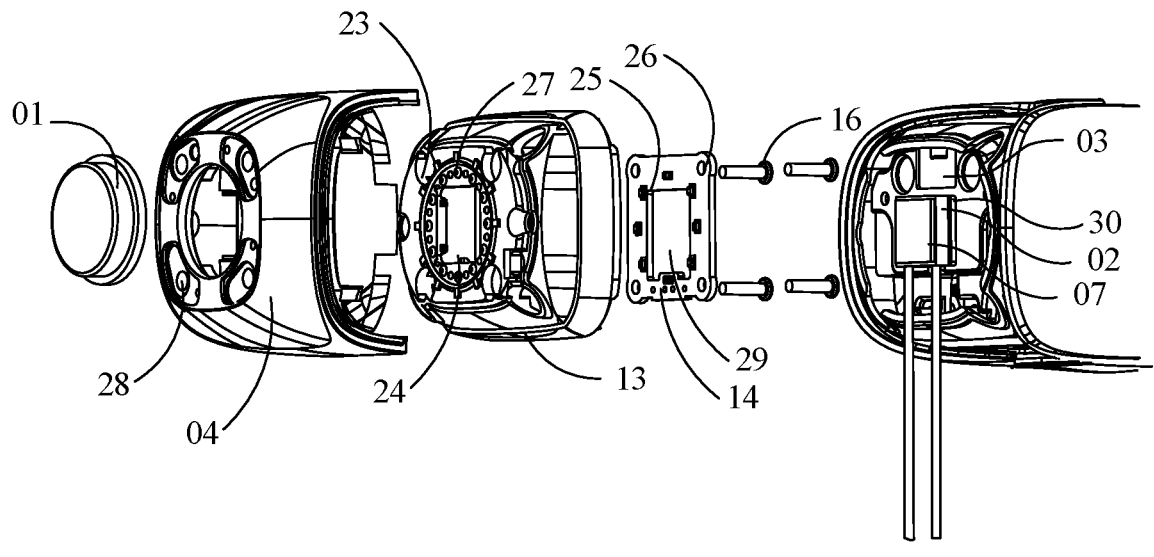
FIG. 18 is an exploded schematic view of the head portion of the skin care assembly according to another embodiment of the present disclosure.
Figure 19:
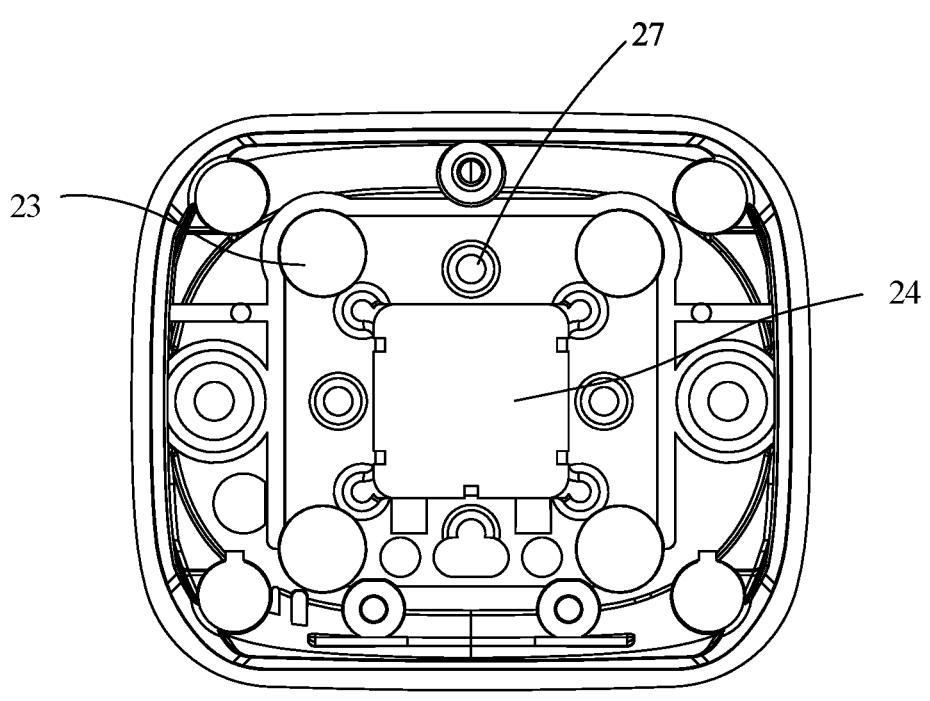
FIG. 19 is a structural schematic view of a side of a light-transmitting plate close to a phototherapy lamp plate of the skin care assembly according to another embodiment the present disclosure.
Figure 20:
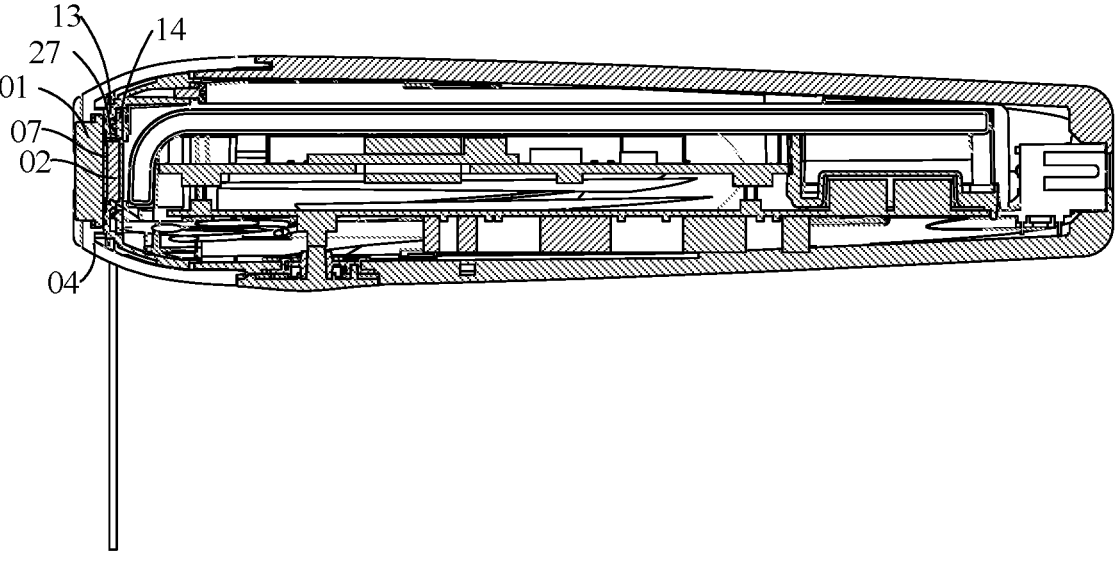
FIG. 20 is a cross-sectional schematic view of the skin care assembly according to another embodiment of the present disclosure.
Figure 21:
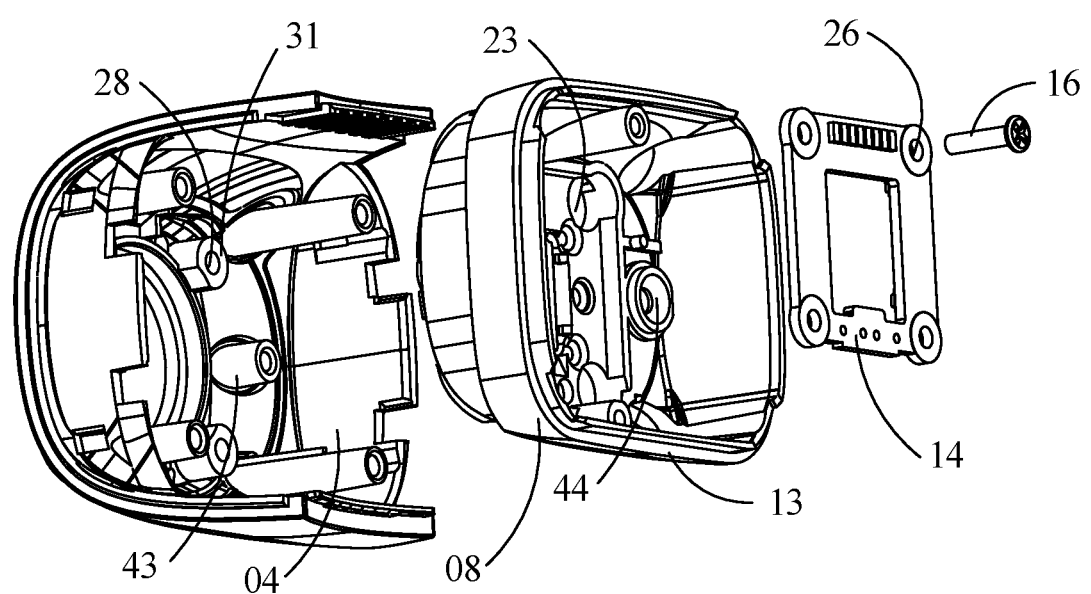
FIG. 21 is an exploded schematic view of the first cover, the light-transmitting plate, the phototherapy lamp plate, and a first bolt of the skin care assembly according to another embodiment of the present disclosure.
Figure 22:
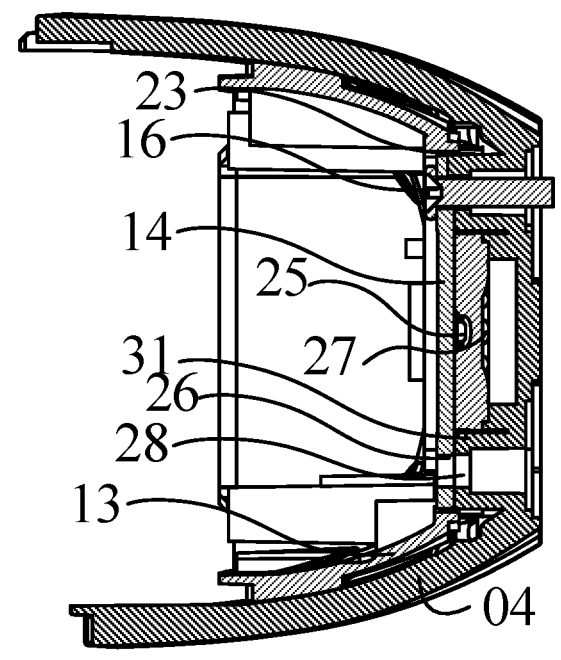
FIG. 22 is a cross-sectional schematic view of an assembly of the first cover, the light-transmitting plate, the phototherapy lamp plate, and the first bolt of the skin care assembly according to another embodiment of the present disclosure.
Figure 23:
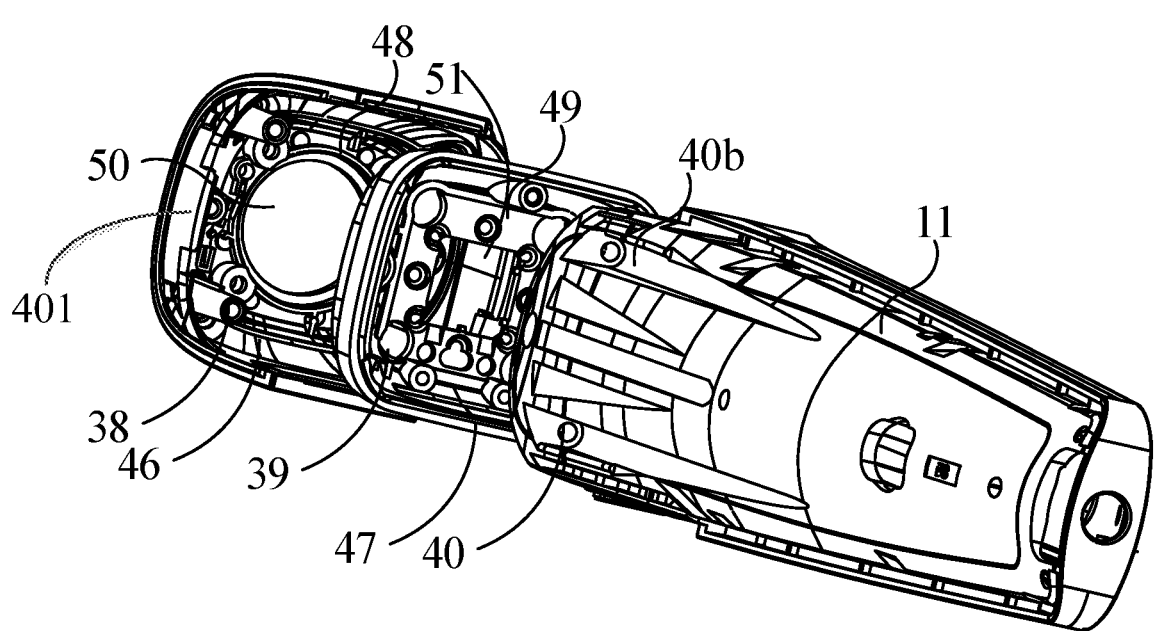
FIG. 23 is a structural schematic view of the first cover, the second cover, and the inner housing of the skin care assembly according to an embodiment of the present disclosure.

FIG. 18 is an exploded schematic view of the head portion of the skin care assembly according to another embodiment of the present disclosure. FIG. 19 is a structural schematic view of a side of a light-transmitting plate close to a phototherapy lamp plate of the skin care assembly according to another embodiment the present disclosure. FIG. 20 is a cross-sectional schematic view of the skin care assembly according to another embodiment of the present disclosure. FIG. 21 is an exploded schematic view of the first cover, the light-transmitting plate, the phototherapy lamp plate, and a first bolt of the skin care assembly according to another embodiment of the present disclosure. FIG. 22 is a cross-sectional schematic view of an assembly of the first cover, the light-transmitting plate, the phototherapy lamp plate, and the first bolt of the skin care assembly according to another embodiment of the present disclosure. FIG. 23 is a structural schematic view of the first cover, the second cover, and the inner housing of the skin care assembly according to an embodiment of the present disclosure.

As shown in FIGS. 18 to 20, the skin care assembly may further include a phototherapy lamp board 14, multiple phototherapy lamps 25 are arranged on a side of the phototherapy lamp board 14 close to the first cover 04, and an escape hole 29 is defined in a center of the phototherapy lamp board 14. The multiple phototherapy lamps 25 are arranged around the escape hole 29, and may exactly be covered by a projection of the cold compress component 01 in a direction perpendicular to the contacting surface 01a. The refrigeration component 02 and the cold-conducting layer 07 may pass through the escape hole 29 to be directly contacted with the cold compress component 01. The phototherapy lamp board 14 is arranged opposite to the heat sink 03, and a side of the phototherapy lamp board 14 without the phototherapy lamps 25 is abutted against and thermally coupled to the heat sink 03. The escape hole 29 has a position-limiting action on a first limiting portion 30 protruding from the heat sink 03, such that the phototherapy lamp board 14 and the heat sink 03 may be fixed relative to each other. The first limiting portion 30 is thermally coupled to the refrigeration component 02.

In some embodiments, the light-transmitting plate 13 may be arranged between the phototherapy lamp plate 14 and the first cover 04. A second through hole 24 is defined in a center of the light-transmitting plate 13 and opposite to the escape hole 29. Several light-transmitting portions 27 are defined around the second through hole 24. The light-transmitting portions 27 are defined corresponding to the phototherapy lamps 25, and may exactly be covered by the projection of the cold compress component 01 in the direction perpendicular to the contacting surface 01a. The light-transmitting portions 27 are covered with light-transmitting materials, and light emitted by the phototherapy lamps 25 may pass through the light-transmitting portions 27 and be mapped to the cold compress component 01. The refrigeration component 02 and the cold-conducting layer 07 may pass through the second through hole 24 to be directly contacted with the cold compress component 01. The second through hole 24 may have a position-limiting action on the refrigeration component 02. The phototherapy lamp board 14 defines multiple first fixing holes 26. The first fixing holes 26 are located opposite to third fixing holes 28d (referring to FIG. 9) in the first cover 04, and configured to fix the phototherapy lamp board 14 relative to the first cover 04.

As shown in FIGS. 21 and 22, the phototherapy lamp board 14, the first cover 04, and the light-transmitting plate 13 may be relatively fixed in a way of snapping, latching, mortising, or thread-bolt connecting. A connection manner provided in the embodiment is the thread-bolt connecting. An inner wall of the first fixing hole 26 and an inner wall of the third fixing hole 28d also define threads corresponding to a first bolt 16. Several first bolts 16 may pass through the first fixing holes 26 and the third fixing holes 28d to have the phototherapy lamp board 14 and the first cover 04 relatively fixed.

In some embodiments, the light-transmitting plate 13 defines several second fixing holes 23, and the number of the second fixing holes 23 is the same as the number of the first fixing holes 26, the number of the third fixing holes 28 d, and the number of the first bolts 16. A side of the first cover 04 close to the light-transmitting plate 13 defines a sinking groove 31, and a shape and an outer diameter of the sinking groove 31 are approximately the same as those of the second fixing holes 23. That is, the second fixing holes 23 may have a position-limiting action on the sinking groove 31. The third fixing hole 28d penetrated through the sinking groove 31, such that the phototherapy lamp board 14, the light-transmitting board 13, and the first cover 04 may be relatively fixed by the first bolts 16 in a sequence as above.

In some embodiments, the phototherapy lamps 25 may be LED light-emitting lamp beads, and light emitted by the phototherapy lamps 25 exiting to the cold compress component 01 through the light-transmitting portions 27 may appear as red light, which may generate an effect of performing a phototherapy for the skin. Further, the phototherapy lamps 25 may also have other functions, such as a hair removal.

In some embodiments, the light-transmitting materials covered on the light-transmitting portions 27 may be mostly organic or inorganic materials with good light-transmitting performances, such as various optical plastics, silicate glasses, or the like.

In some embodiments, the light-transmitting plate 13 may not be disposed between the phototherapy lamp plate 14 and the first cover 04, and the light emitted by the phototherapy lamps 25 may be directly mapped to the cold compress component 01.

Figure 15:
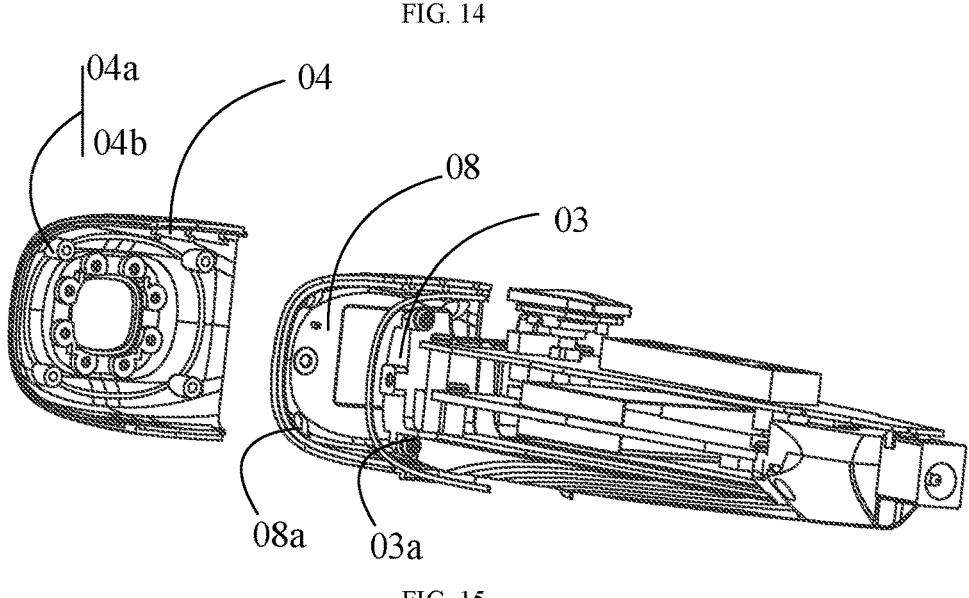
FIG. 15 is a schematic view of an assembly of the first cover, a second cover, and a heat sink of the skin care assembly according to an embodiment of the present disclosure.
Figure 16:
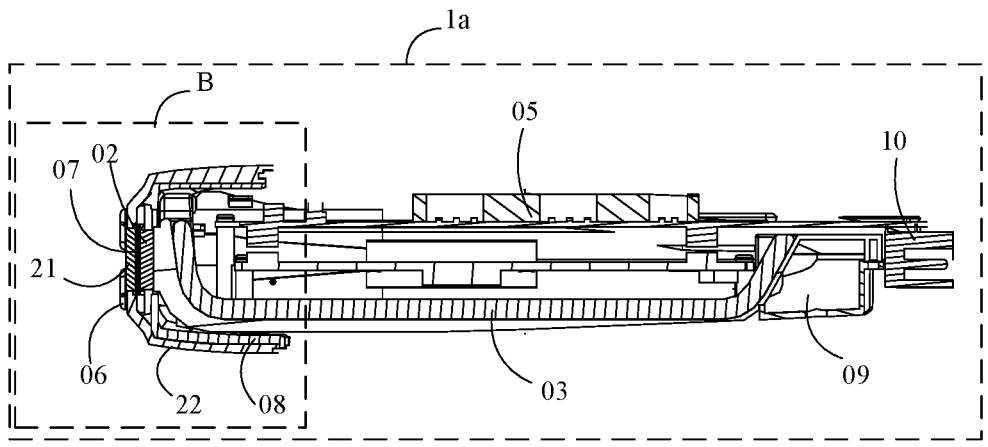
FIG. 16 is a cross-sectional schematic view of the skin care assembly according to an embodiment of the present disclosure.
Figure 17:
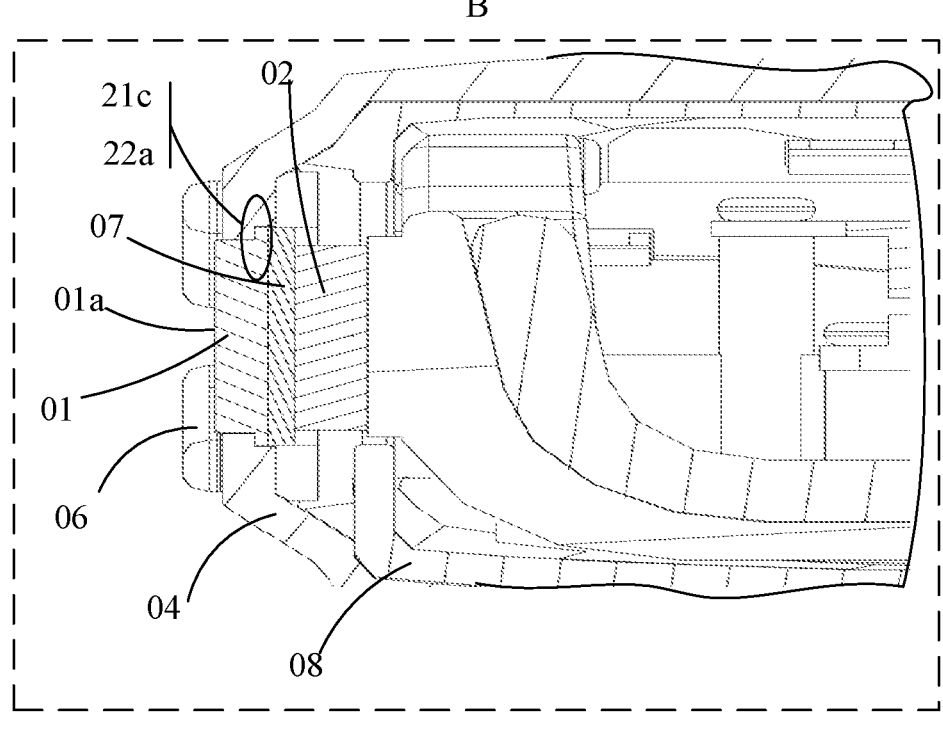
FIG. 17 is a partial enlarged view of a position B in FIG. 16.

FIG. 15 is a schematic view of an assembly of the first cover, a second cover, and a heat sink of the skin care assembly according to an embodiment of the present disclosure. FIG. 16 is a cross-sectional schematic view of the skin care assembly according to an embodiment of the present disclosure. FIG. 17 is a partial enlarged view of a position B in FIG. 15.

In some embodiments, the skin care assembly 1 includes a cold compress component 01, a refrigeration component 02, a heat sink 03, a first cover 04, a pulse-generating circuit 05, and an electrode 06. The cold compress component 01 includes a contacting surface 01a and a conducting surface 01b, and the contacting surface 01a is configured to directly contact the skin. A refrigeration side of the refrigeration component 02 is thermally coupled to the conducting surface 01b of the cold compress component 01 to reduce a temperature of the cold compress component 01. The heat sink 03 is thermally coupled to a heat-generating side of the refrigeration component 02 to dissipate heat from the refrigeration component 02. The first cover 04 is configured to relatively fix the cold compress component 01 to the heat sink 03, and at least partially wrap or accommodate the cold compress component 01 and the heat sink 03. The pulse-generating circuit 05 is arranged on a side of the heat sink 03 facing away from the refrigeration component and configured to generate an electric/magnetic pulse. The electrode 06 is relatively fixed to the first cover 04 and protrudes relative to the first cover 04. The electrode 06 is connected to the pulse-generating circuit. When the electrode 06 directly contacts the skin, the pulse-generating circuit 05 may generate the electric/magnetic pulse to maintain the skin.

In some embodiments, a cold-conducting layer may be arranged between the heat-generating side of the refrigeration component 02 and the heat sink 03, and filled with a thermally conductive silicone grease, so as to have a more sufficient heat transfer and also make a control for the temperature smoother. In this way, a feeling of the skin may be more comfortable.

In the care assembly 1 in the embodiment, both the cold compress component 01 and the electrode 06 are fixed on the first cover 04, such that the cold compress component 01 and the electrode 06 may be better fixed, increasing a structural stability thereof. In addition, both the refrigeration component 02 and the pulse-generating circuit 05 are arranged on the heat sink 03, and the pulse-generating circuit 05 is located on the side of the heat sink 03 facing away from the refrigeration component, which improves the heat-dissipating efficiency of the care component 1 with reducing an interference of the heat generated by the refrigeration component 02 and the pulse-generating circuit 05 on the cold compress component 01. The electrode 06 is fixed on the first cover 04, such that a structure for mounting the electrode 06 may be avoided to be processed on a component such as the cold compress component 01, reducing a processing cost accordingly.

Specifically, as shown in FIG. 15, the first cover 04 may include two side surfaces, i.e., an outer side surface and an inner side surface. The outer side surface is exposed to air and is configured to fix the electrode 06 and the cold compress component 01, and the inner side surface is configured to wrap or accommodate the refrigeration component 02 and partially wrap or accommodate the heat sink 03 and the cold compress component 01. In some embodiments, four first mounting holes 04b are defined in the inner side surface of the first cover 04 and configured to fix the first cover 04. The heat sink 03 includes a first end, and a first end of the heat sink 03 defines four second mounting holes. After the electrode 06 and the cold compress component 01 are mounted on the first cover 04, the first mounting holes 04b in the cover body 04 are assembled corresponding to the four second mounting holes in the heat sink 03 and fixed by screws. Subsequently, the first end of the heat sink 03 is wrapped or accommodated by the first cover 04 in an inner side of the first cover 04. The heat-generating side of the refrigeration component 02 is connected and thermally coupled to the first end of the heat sink 03, and both the heat-generating side of the refrigeration component 02 and the first end of the heat sink 03 are wrapped or accommodated by the first cover 04. The refrigeration side of the refrigeration component 02 is thermally coupled to the conducting surface 01b of the cold compress component 01, and both the refrigeration side of the refrigeration component 02 and the conducting surface 01b of the cold compress component 01 are wrapped or accommodated by the first cover 04. The contacting surface 01a of the cold compress component 01 and the electrode 06 are both located on an outer side of the first cover 04, such that the skin care assembly 1 may perform an electromagnetic pulse therapy for the skin through the electrode 06 during operating while also protecting the skin by reducing the temperature of the skin through the cold compress component 01, so as to improve a skin care effect of the skin care assembly 1 for the skin. A first accommodating cavity is defined between the first end of the heat sink 03 and a second end of the heat sink 03. The second end of the heat sink 03 described above is an end of the heat sink 03 connected to the first end of the heat sink 03 and away from the heat-generating side of the refrigeration component 02. A supporting frame is arranged in the first accommodating cavity. The pulse-generating circuit 05 is fixed on the supporting frame of heat sink 03. When the skin care assembly 1 is in operating, the heat generated by the refrigeration component 02 and the pulse-generating circuit 05 is directly conducted to the heat sink 03 and dissipated through the heat sink 03 based on a high heat-dissipating performance of the heat sink 03.

Specifically, as described above, the first cover 04 may include the two side surfaces, i.e., the outer side surface and the inner side surface. The inner side surface and the outer side surface are fluidly communicated to each other through the first opening 50. A mounting platform is arranged on the outer side of the first cover 04. The cold compress component 01 is fixed on the mounting platform in the outer side of the first cover 04 through being pressed by the electrode 06. In this case, the inner side of the first cover 04 defines a first receiving cavity 401. A part of components including the heat sink 03 of the skin care assembly 1 are wrapped or accommodated by the first cover 04 or partially wrapped or accommodated in the first receiving cavity 401. The conducting surface 01b of the cold compress component 01 passes through the first opening 50 between the inner side surface and outer side surface of the first cover 04 and abuts against one side of the heat sink 03.

Figure 6:
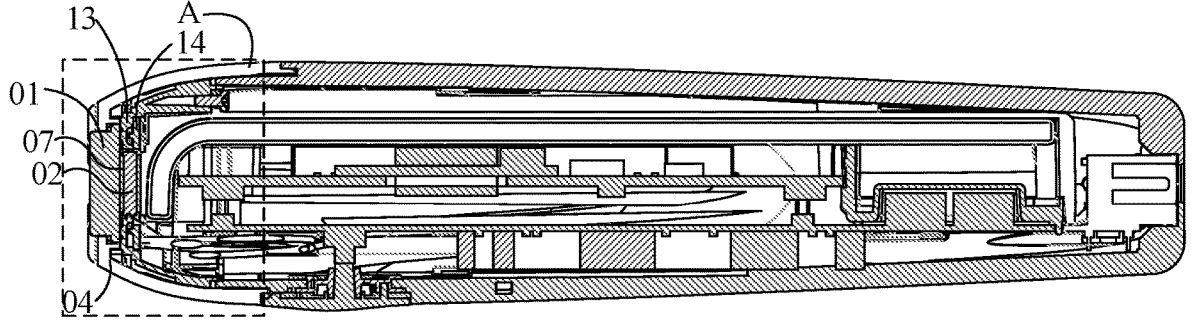
FIG. 6 is a cross-sectional schematic view of the skin care assembly according to an embodiment of the present disclosure.
Figure 7:
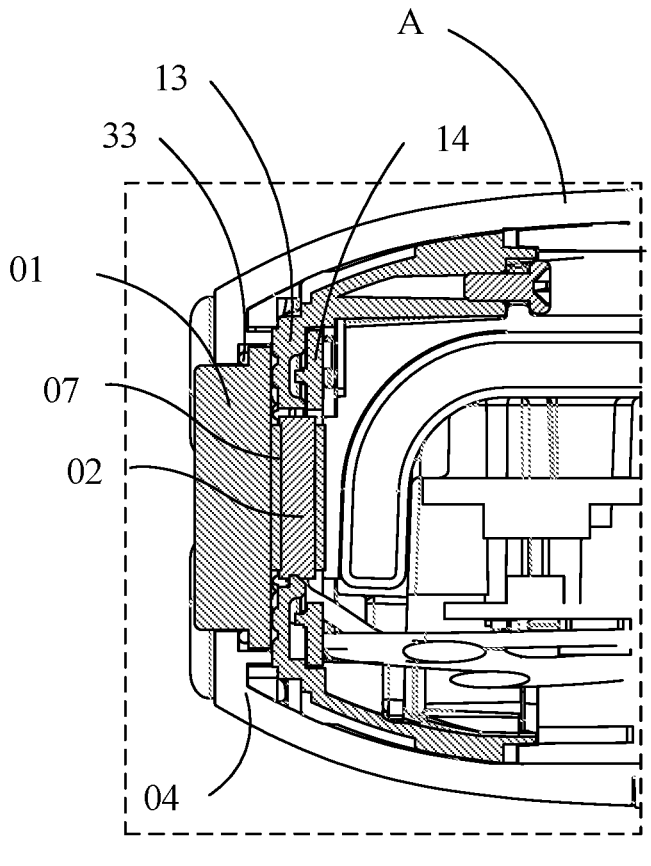
FIG. 7 is a partial enlarged view of a position A in FIG. 6.
Figure 8:
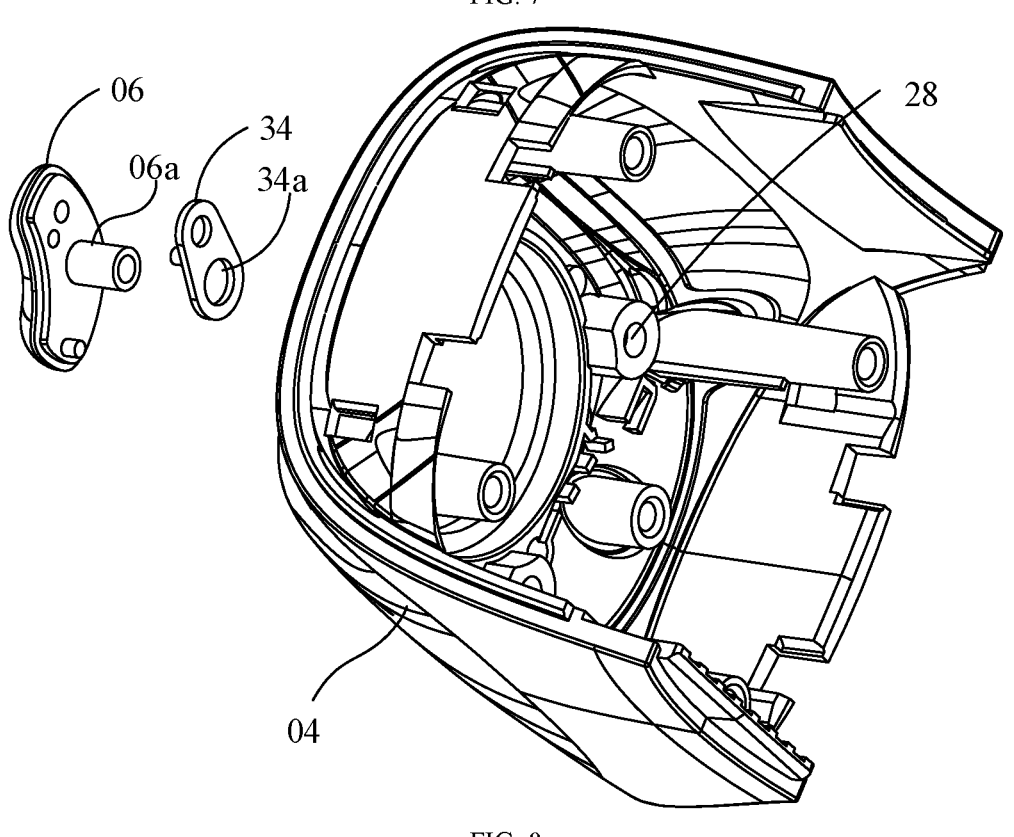
FIG. 8 is an exploded schematic view of an electrode and a first cover of the skin care assembly in a direction according to some embodiments of the present disclosure.
Figure 9:
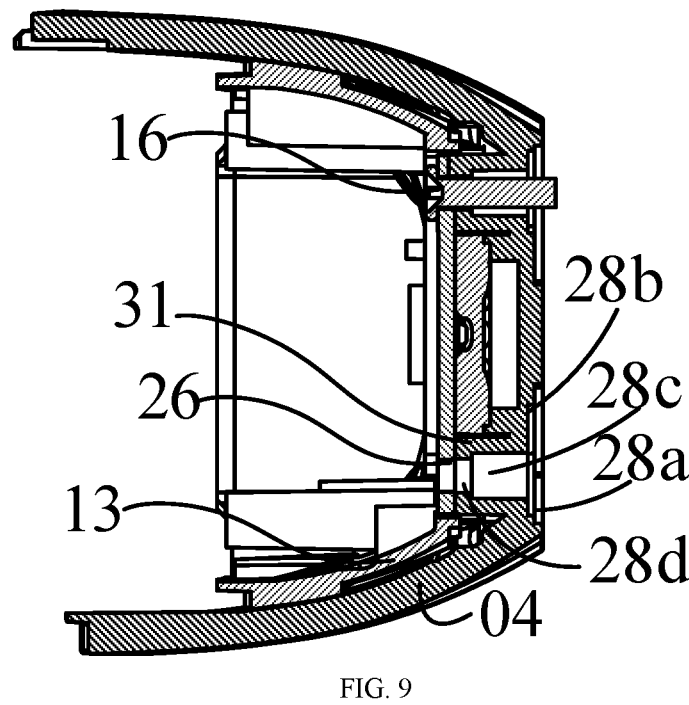
FIG. 9 is a cross-sectional schematic view of an assembling position of the electrode of the skin care assembly according to some embodiments the present disclosure.

FIG. 6 is a cross-sectional schematic view of the skin care assembly according to an embodiment of the present disclosure. FIG. 7 is a partial enlarged view of a position A in FIG. 6. FIG. 8 is an exploded schematic view of an electrode and a first cover of the skin care assembly in a direction according to some embodiments of the present disclosure. FIG. 9 is a cross-sectional schematic view of an assembling position of the electrode of the skin care assembly according to some embodiments the present disclosure.

Specifically, as shown in FIGS. 4, 8 and 9, in the embodiment, the electrode 06 is configured in a crescent shape and has two special ends. An end of the two special ends is a body portion configured to maintain the skin by adopting the electric/magnetic pulse during the electrode 06 being in operating. The other end of the two special ends is a fixing portion. The fixing portion is connected to the first cover 04, such that the electrode 06 may be fixed on the mounting platform in the outer side of the first cover 04. The fixing portion faces towards the mounting platform in the outer side of the first cover 04 during being mounted. The fixing portion includes at least one mounting column 06a. At least one mounting hole 28c is defined on the mounting platform of the first cover 04. The electrode 06 may be fixed to the first cover 04 through the at least one mounting column 06a being mounted in the at least one mounting hole 28c.

In some embodiments, a height of the electrode 06 protruding relative to the first cover 04 is between 0 mm-20 mm.

In some embodiments, a first sinking hole 28a is defined in the mounting platform of the first cover 04, and slightly lower than the mounting platform. The first sinking hole 28a has a shape corresponding to the shape of the electrode 06 and is configured to fix the electrode 06 on the mounting platform and preventing the electrode 06 from being shaked or shifted.

Further, in order to better fix the electrode 06 and prevent outside water and oil from infiltrating a machine body, a gasket 34 for sealing and absorbing a shock may be arranged between the first cover 04 and the electrode 06. A second sinking hole 28b configured to accommodate the gasket 34 is defined in the second sinking hole 28b of the mounting platform. The second sinking hole 28b has a shape corresponding to a shape of the gasket 34. At least one third through hole 34a is defined in the gasket 34. The number of the at least one third through hole 34a matches the number of the at least one mounting column 06a, and a shape of the at least one third through hole 34a is adapted to a cross-sectional shape of the at least one mounting column 06a, such that the at least one mounting column 06a passes through the at least one third through hole 34a to fix the gasket 34 between the first cover 04 and the electrode 06.

In some embodiments, other corresponding fixed facilities may also be arranged on the gasket 34, the electrode 06, and the first cover 04 to prevent the gasket 34 from being shifted.

In some embodiments, the gasket 34 may be made of a material such as a silica gel, etc., which may be capable of occurring an elastic deformation and have a greater friction coefficient.

In some embodiments, from an aesthetic and economical view, the shape of the gasket 34 may be adapted to the shape of the electrode 06, and has a size less than a size of the shape of the electrode 06.

As shown in FIGS. 5 and 17, the cold compress component 01 is located in the first opening 50 of the first cover 04. The cold compress component 01 has a first radial size and a second radial size different from the first radial size at positions corresponding to different thicknesses. The first opening 50 has a third radial size and a fourth radial size different from the third radial size at positions corresponding to different depths. A portion of the cold compress component 01 having the first radial size is closer to the cold-conducting layer 07 than a portion of the cold compress component 01 having the second radial size. A portion of the first opening 50 having the third radial size is closer to the cold-conducting layer 07 than a portion of the first opening 50 having the fourth radial size. The first radial size is less than the third radial size, the second radial size is less than the fourth radial size, and the second radial size is greater than the third radial size.

Specifically, a first stepped surface 21c is arranged between the portion having the first radial size and the portion having the second radial size of the cold compress component 01. A second stepped surface 22a is arranged between the portion having the third radial size and the portion having the fourth radial size of an inner side of the first opening 50 of the first cover 04. An outer side of the first opening 50 of the first cover 04 is arranged with the mounting platform.

The electrode 06 is mounted on the mounting platform on the outer side of the first cover 04, and is configured to maintain the skin. The refrigeration component 02, the cold-conducting layer 07, and the cold compress component 01 abut against the first end of the heat sink 03 in sequence, and are fixed between the first cover 04 and the first end of the heat sink 03 through the second stepped surface 22a in the inner side of the first cover 04 abutting against and being attached to the first stepped surface 21c of the cold compress component 01. In addition, the contacting surface 01a of the cold compress component 01 passes through the first opening 50 of the first cover 04 and is located on the outer side of the first cover 04, configured to assist the electrode 06 to maintain the skin.

As shown in FIGS. 4 to 7, in order to better fix the cold compress component 01 and prevent the outside water and oil from infiltrating the machine body, a first sealing component 33 for sealing and absorbing the shock may be arranged between the first opening 50 of the first cover 04 and the cold compress component 01. The first sealing component 33 is arranged between the first stepped surface 21*c* and the second stepped surface 22*a*. When the cold compress component 01 abuts against the first opening 50 of the first cover 04, the first sealing component 33 may be deformed by a force, such that an inside of the machine body of the skin care assembly 1 may be isolated from an external environment. The first sealing component 33 may serve as a buffer when the machine body is bumped or dropped.

In some embodiments, a shape of the first sealing component 33 may be adapted to a shape of the first stepped surface 21*c*.

In some embodiments, other corresponding fixed facilities may also be arranged between the first sealing component 33, the cold compress component 01, and the first cover 04 to prevent the first sealing component 33 from being shifted.

In some embodiments, the first sealing component 33 may be made of the material such as the silica gel, etc., which may be elastically deformed and have the greater friction coefficient.

Figure 10:
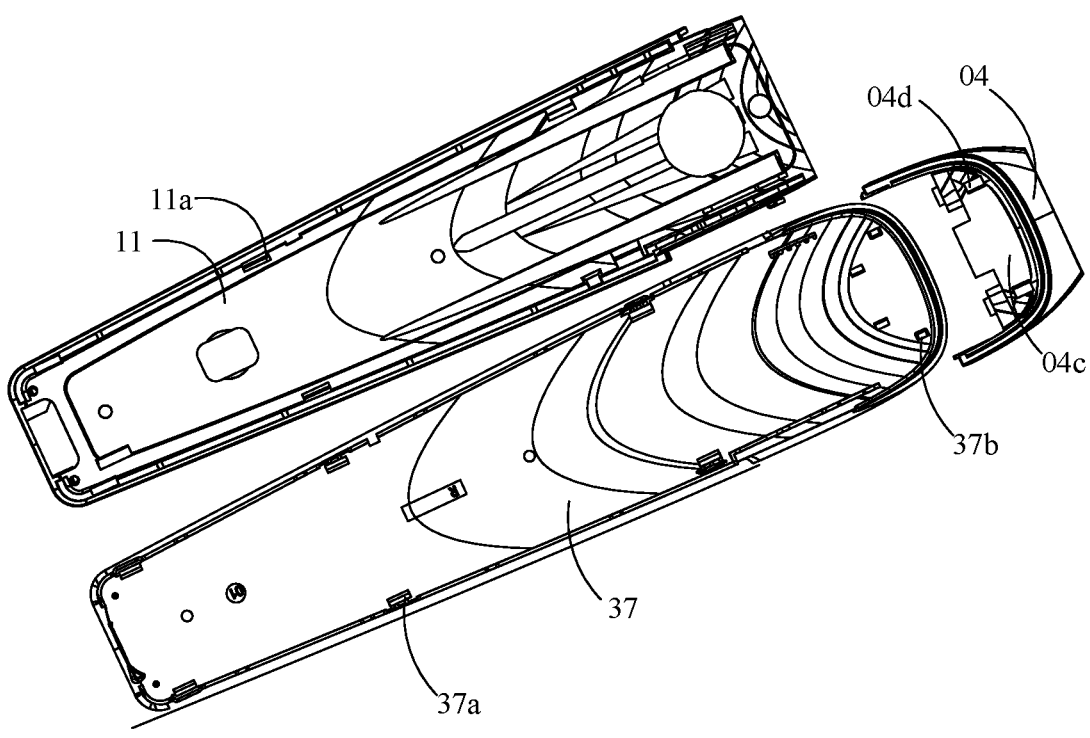
FIG. 10 is a structural schematic view of the first cover and an inner housing of the skin care assembly in a direction according to some embodiments the present disclosure.
Figure 11:
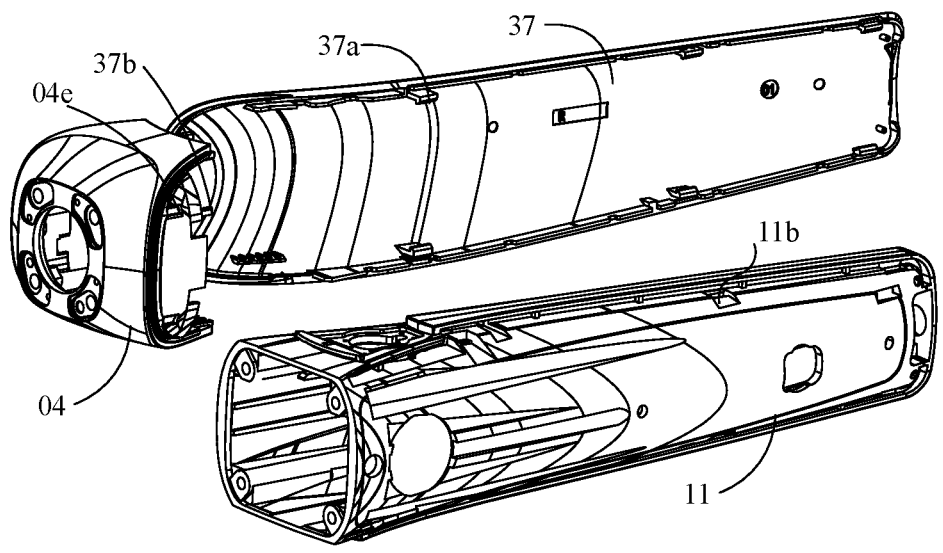
FIG. 11 is a structural schematic view of the first cover and the inner housing of the skin care assembly in another direction according to some embodiments the present disclosure.

FIG. 10 is a structural schematic view of the first cover and an inner housing of the skin care assembly in a direction according to some embodiments the present disclosure. FIG. 11 is a structural schematic view of the first cover and the inner housing of the skin care assembly in another direction according to some embodiments the present disclosure.

As shown in FIGS. 10 and 11, the skin care assembly 1 provided in some embodiments of the present disclosure may further include the inner housing 11 and an outer housing 37. The skin care assembly 1 may be at least partially arranged in the inner housing 11. For example, the heat sink 03 is partially arranged in the inner housing 11 and fixed relative to the inner housing 11, and the inner housing 11 is partially arranged in an inner side of the outer housing 37. A second fastener 37*b* is fixed on the outer housing 37, and a first fastener 04*d* is fixed on the first cover 04. The second fastener 37*b* is snapped to the first fastener 04*d*. The first fastener 04*d* is fixed on the first cover 04, and the second fastener 37*b* is fixed on the outer housing 37, such that it may be more convenient for the skin care assembly 1 to be mounted and aligned and have an accessory replaced when the skin care assembly 1 is assembled.

In some embodiments, a part of the second fastener 37*b* is arranged on a side of the outer housing 37 close to a thermally coupling surface of the heat sink 03, i.e., a side where a cavity opening of an empty cavity for accommodating the heat sink 03 of the outer housing 37 is located, and close to a side wall 04*c* of the first cover 04. The first cover 04 includes the side wall 04*c* corresponding to the outer housing 37, and the first fastener 04*d* is arranged on two side walls 04*c* of the first cover 04.

In some embodiments, the first fastener 04*d* may define a bayonet, an edge of the bayonet may be arranged with an inclined surface 04*e*. The second fastener 37*b* may include a hook. Under a guide of the inclined surface 04*e*, the hook of the second fastener 37*h* may enter into the bayonet of the first fastener 04*d* to complete a snap connection. In this way, the side walls 04*c* of the first cover 04 may be assembled with the outer housing 37.

In some embodiments, the side walls 04*c* may be arranged with multiple first fasteners 04*d* and inclined surfaces 04*e*. The inner side of the outer housing 37 may be also arranged with the second fasteners 37*b* corresponding to the first fasteners 04*d* in the number and positions. No specific restrictions are made herein.

In some embodiments, the first fasteners 04*d* on the side walls 04*c* and the second fasteners 37*b* on the inner side of the outer housing 37 may be correspondingly arranged asymmetrically. For example, an upper side and a lower side are distinguished based on the button 12, the numbers of the first fasteners 04*d* and the second fasteners 37*b* close to the upper side are different from those of the ones close to the lower side, such that front and back for mounting of the side walls 04*c* of the first cover 04 and front and back for mounting of the outer housing 37 may be clearly distinguished, and a foolproof effect may be achieved.

As shown in FIGS. 10 and 11, the skin care assembly 1 provided in some embodiments of the present disclosure further includes a third fastener 11*b* and a fourth fastener 37*a*. Fourth fasteners 37*a* are fixed on an edge of the outer housing 37, and third fasteners 11*b* are fixed on edges of two side surfaces of the inner housing 11. The third fasteners 11*b* are snapped to the fourth fasteners 37*a*. The third fasteners 11*b* are arranged on the inner housing 11, and the fourth fasteners 37*a* are arranged on the outer housing 37, such that it may be more convenient for the skin care assembly 1 to be mounted and aligned and have the accessory replaced when the skin care assembly 1 is assembled.

In some embodiments, the third fasteners 11*b* are arranged on the edges of the two side surfaces of the inner housing 11, generally by arranging several third fasteners 11*b* from a head portion of the inner hosing 11 to a tail of the inner housing 11. The fourth fasteners 37*a* are arranged on the inner side of the outer housing 37 at positions corresponding to the third fasteners 11*b*. Since a shape of the outer housing 37 fit for shapes of the two side surfaces of the inner housing 11, several third fasteners 11*b* are arranged along the edge of the outer housing 37 from a head portion of the outer housing 37 to a tail of the outer housing 37.

In some embodiments, the third fasteners 11*b* may include bayonets, edges of the bayonets may be arranged with inclined surfaces. The second fasteners 37*b* may include hooks. Under guides of the inclined surfaces, the hooks of the second fasteners 37*b* may enter into the bayonets of the first fasteners 11*b* to complete a snap connection. In this way, the two side surfaces of the inner housing 11 may be assembled with the outer housing 37.

In some embodiments, the edges of the two side surfaces of the inner housing 11 may be arranged with multiple third fasteners 11*b* and inclined surfaces. The inner side of the outer housing 37 may be also arranged with the fourth fasteners 37*a* corresponding to the third fasteners 11*b* in the number and positions. No specific restrictions are made herein.

In some embodiments, the third fasteners 11*b* on the edges of the two side surfaces of the inner housing 11 and the fourth fasteners 37*a* on the inner side of the outer housing 37 may be correspondingly arranged asymmetrically. For example, a front side and a rear side are distinguished based on the button 12, the numbers of the third fasteners 11*b* and the inclined surfaces arranged on the edges of the side surfaces of the inner housing 11 on the front side, and the fourth fasteners 37*a* are different from those on the rear side. In this way, front and back for mounting may be clearly distinguished, and the foolproof effect may be achieved.

Figure 24:
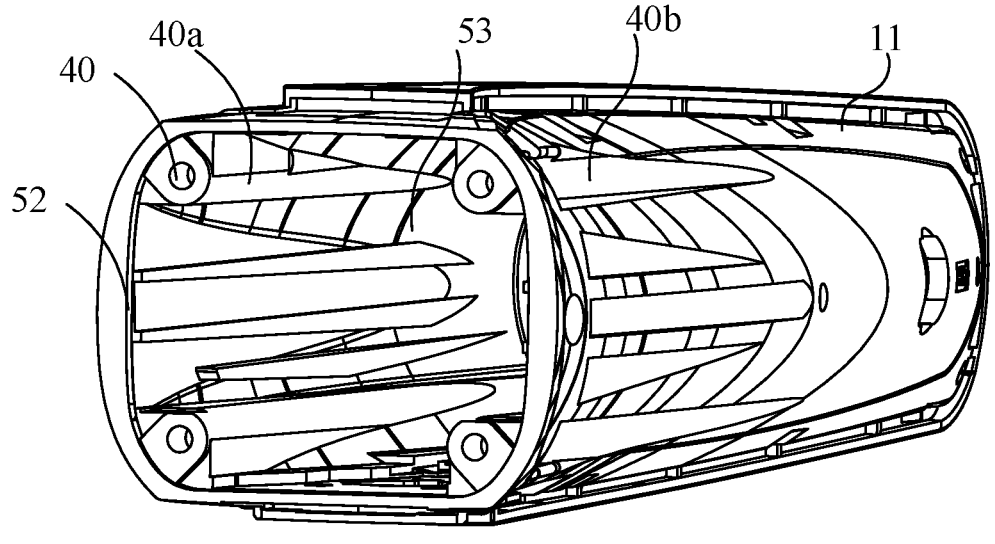
FIG. 24 is a structural schematic view of the inner housing of the skin care assembly according to an embodiment of the present disclosure.
Figure 25:
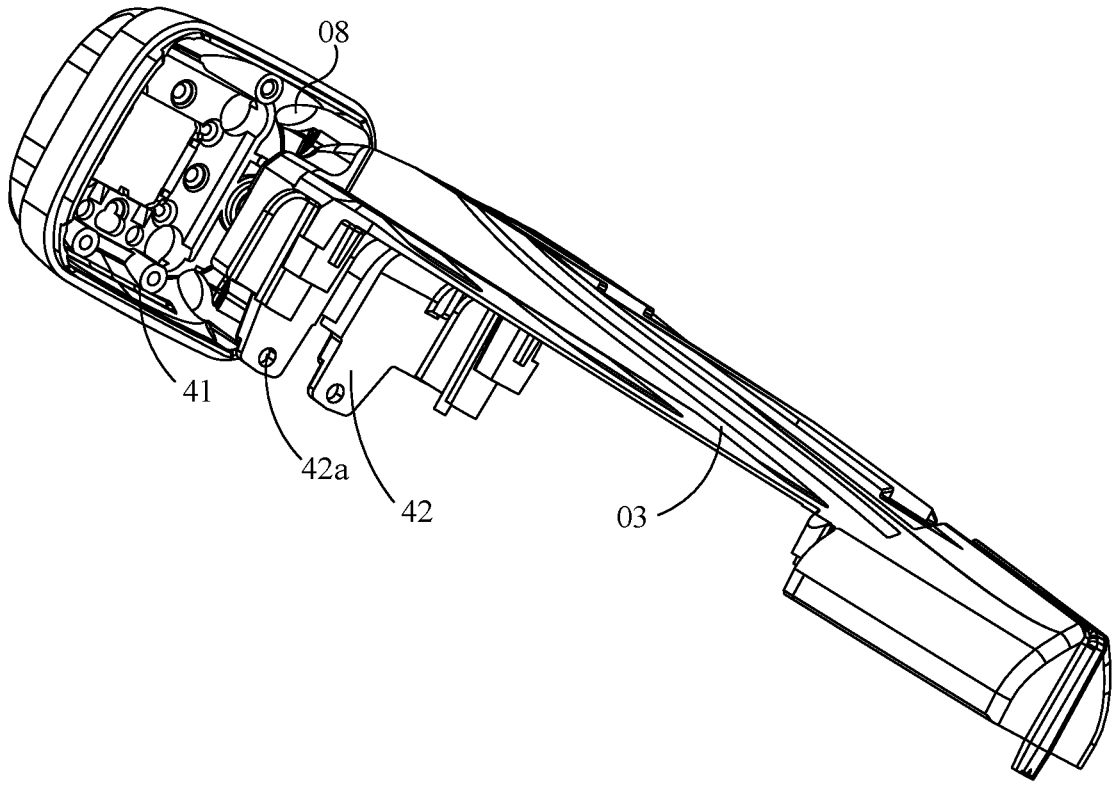
FIG. 25 is a structural schematic view of the second cover and the heat sink of the skin care assembly according to an embodiment of the present disclosure.

FIG. 23 is a structural schematic view of the first cover, the second cover, and the inner housing of the skin care assembly according to an embodiment of the present disclosure. FIG. 24 is a structural schematic view of the inner housing of the skin care assembly according to an embodiment of the present disclosure. FIG. 25 is a structural schematic view of the second cover and the heat sink of the skin care assembly according to an embodiment of the present disclosure.

As shown in FIGS. 23 to 25, in an embodiment of the skin care assembly 1 of the present disclosure, the first cover 04 includes a first panel portion 48 parallel to the contacting surface of the cold compress component 01, and a first side wall extending along a direction from a side edge of the first panel portion 48 towards the heat sink 03, such that the first receiving cavity 401 may be defined in the inner side of the first cover 04. The first opening 50 is defined in the first panel portion 48, the contacting surface of the cold compress component 01 is exposed to an outer side of the first receiving cavity 401 from the first opening 50 to directly contact the skin.

The second cover 08 includes a second panel portion 49 parallel to the first panel portion 48, and a second side wall 47 extending along a direction from a side edge of the second panel portion 49 towards the heat sink 03. A second receiving cavity is defined in the inner side of the second cover 08. The second panel portion 49 defines a second opening 51. The conducting surface of the heat sink 03 is exposed to the second receiving cavity through the second opening 51, so as to be thermally coupled to the refrigeration component 02.

In some embodiments, the second cover 08 is embedded in the first receiving cavity 401 of the first cover 04 and fixed to the first cover 04. The cold compress component 01 is fixed between the first panel portion 48 of the first cover 04 and the second panel portion 49 of the second cover 08.

In some embodiments, the skin care assembly 1 in some embodiments of the present disclosure further includes a first mounting column 41 and defines a first mounting hole 42*a*. The first mounting column 41 is arranged in the second receiving cavity of the second cover 08. A mounting ear 42 extends radially from a side edge of the heat sink 03, the first mounting hole 42*a* is defined in the mounting ear 42. The number of the mounting ear 42 corresponds to the number of the first mounting column 41. An end of the heat sink 03 thermally coupled to the refrigeration component 02 is partially embedded in the second receiving cavity of the second cover 08 and fixed to the second cover 08.

In some embodiments, an end of the first mounting column 41 close to the first mounting hole 42*a* defines a threaded hole, and a first stud penetrates into the threaded hole at the end of the first mounting column 41 from the first mounting hole 42*a* of the mounting ear 42 to screw the heat sink 03 to the second cover 08.

In some embodiments, the first stud passes through the first mounting hole 42*a* and be connected to the threaded hole at the end of the first mounting column 41 from a side of the mounting ear 42 facing away from the second cover 08.

In some embodiments, the skin care assembly 1 in some embodiments of the present disclosure further defines an accommodating cavity 53 and an opening 52. The accommodating cavity 53 is defined in the inner side of the inner housing 11, and extends from the head portion of the inner housing 11 to the tail of the inner housing 04. The opening 52 is defined at an end of the accommodating cavity 53 close to the refrigeration component 02. The heat sink 03 is partially embedded in the accommodating cavity 53 through the opening 52. The end of the heat sink 03 thermally coupled to the refrigeration component 02 is partially exposed to an outer side of the accommodating cavity 53 through the opening 52, and a portion of the heat sink 03 partially exposed to the outer side of the accommodating cavity 53 through the opening 52 is partially embedded in the first receiving cavity 401 of the first cover 04.

In some embodiments, the skin care assembly 1 in some embodiments of the present disclosure further includes a second mounting column 38, and defines a first through hole 39 and a second mounting hole 40. The second mounting column 38 is arranged in the first receiving cavity 401 of the first cover 04, the first through hole 39 corresponding to the second mounting column 38 is defined in the second receiving cavity of the second cover 08, and the second mounting hole 40 corresponding to the second mounting column 38 is defined in the inner housing 11.

In some embodiments, a diameter of the first through hole 39 is close to and slightly greater than a diameter of the second mounting column 38.

In some embodiments, the second mounting column 38 may be arranged in the first receiving cavity 401 of the first cover 04 at a transiting position between the first panel portion 48 and the first side wall 46. The first through hole 39 may be arranged in a transiting position between the second panel portion 49 and the second side wall 47, so as to cooperate with the second mounting hole 40. The second mounting hole 40 is defined in a wall of the accommodating cavity of the inner housing 11 and close to the opening 52.

In some embodiments, a mounting rib 40*a* is arranged in the accommodating cavity 53 of the inner housing 11 and extends from the opening 52 to a tail of the accommodating cavity 53. A mounting groove 40*b* recessed along a direction towards the accommodating cavity 53 is defined in an outer side of the inner housing at a position corresponding to the mounting rib 40*a*. Due to existence of the mounting rib 40*a* and the mounting groove 40*b*, the second mounting hole 40 is close to a top end of the second mounting column 38 and exposed to an end of the mounting rib 40*a* close to the opening 52, and a bottom of the second mounting hole 40 is exposed to an end of the mounting groove 40*b* close to the opening 52.

In some embodiments, an end of the second mounting column 38 close to the second mounting hole 40 defines a threaded hole, and a second stud may penetrate into a top end of the second mounting hole 40 and pass out a bottom end of the second mounting hole 40, and be screwed to the threaded hole in the end of the second mounting column 38 passing through the first through hole 39, such that the first cover 04 and the inner housing 11 are fixed.

As shown in FIG. 21, the skin care assembly 1 in some embodiments of the present disclosure further includes a third mounting column 43, and defines a third mounting hole 44. The third mounting column 43 is arranged in the first receiving cavity 401 of the first cover 04, and the third mounting hole 44 corresponding to the third mounting column 43 is defined in the second panel portion 49 of the second cover 08. An end of the third mounting column 43 close to the third mounting hole 44 defines a threaded hole. A third stud may pass through the third mounting hole 44 and be screwed to the threaded hole in the end of the third mounting column 43, such that the second cover 08 may be fixed to the first receiving cavity 401 of the first cover 04. In this way, the cold compress component 01 may be fixed to the first receiving cavity 401 of the first cover 04, and located between the first cover 04 and the second cover 08.

In some embodiments, the third mounting hole 44 penetrates through the second panel portion 49 and fluidly communicate to the second receiving cavity of the second cover 08. The conducting surface of the cold compress component 01 may be exposed through the second through hole 24 and thermally coupled to the refrigeration component 02.

Figure 26:
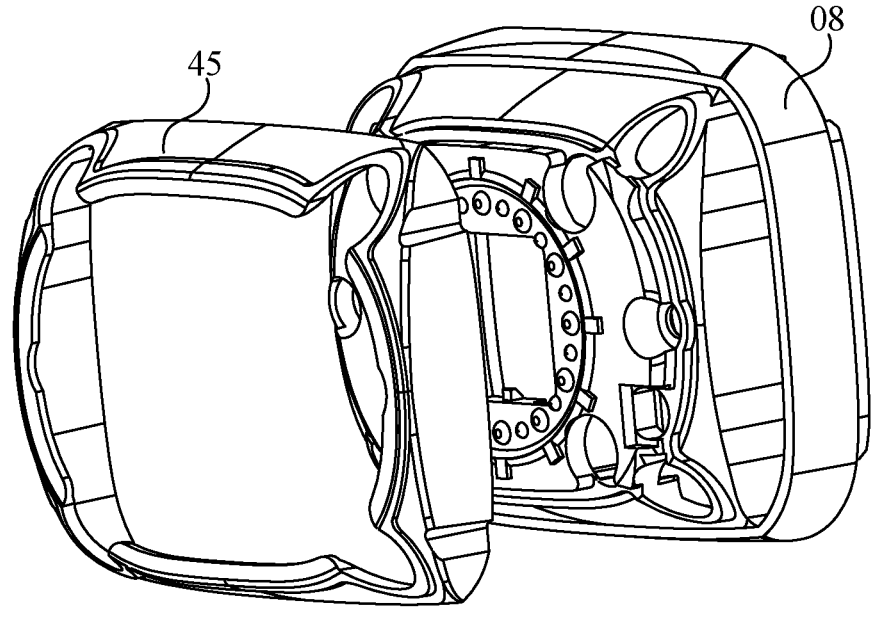
FIG. 26 is a structural schematic view of a second sealing component and the second cover of the skin care assembly according to an embodiment of the present disclosure.

FIG. 26 is a structural schematic view of a second sealing component and the second cover of the skin care assembly according to an embodiment of the present disclosure. As shown in FIG. 26, the skin care assembly 1 in some embodiments of the present disclosure may further include a second sealing component 45 arranged on the second cover 08. The second sealing component 45 is attached to a surface of the transiting portion between the second panel portion 49 and the second side wall 47 of the second cover 08 and tightly attached to the second cover 08. When the second cover 08 and the first cover 04 are assembled, the second sealing component 45 may be deformed due to being extruded by the first cover 04, such that a gap between the second cover 08 and the first receiving cavity 401 of the first cover 04 may be blocked, preventing water and oil from entering into the second receiving cavity of the second cover 08 and affecting a stability of an interior circuit.

In some embodiments, a material of the second sealing component 45 may be an elastic material such as the silica gel, a latex, or the like, and may also be a poured liquid glue.

In some embodiments, the skin care assembly 1 further includes the second cover 08, at least partially located between the first cover 04 and the heat sink 03. The second cover 08 is fixed to the heat sink 03, and the cover 04 is fixed to the second cover 08. The cold compress component 01 tightly presses the cold-conducting layer 07 and the refrigeration component 02 against the heat sink 03 in a first direction.

The second cover 08 is sleeved in the inner side of the first cover 04 and is at least partially located between the first cover 04 and the heat sink 03, and configured to limit a shift of the heat sink 03 in the first direction. The first direction mentioned herein is a direction perpendicular to both the first cover 04 and the second cover 08. Four first positioning holes corresponding to the first mounting holes and the second mounting holes are defined in the second cover 08. Four positioning columns 04a are defined in the inner side of the first cover 04. The first mounting holes 04b of the first cover 04 are defined in the four positioning columns 04a. During mounting, the four positioning columns on the first cover 04 pass through the first positioning holes in the second cover 08 and abut against the second positioning hole in the heat sink 03, and are finally fixed by means of screws. In this way, the second cover 08 may be fixed between the first cover 04 and the heat sink 03. The cold compress component 01 which has been fixed on the first cover 04 passes through the first cover 04 and presses the cold-conducting layer 07 and the refrigeration component 02 tightly to the heat sink 03 along the direction perpendicular to both the first cover 04 and the second cover 08.

In some embodiments, the second cover body 08 further defines a limiting hole. The limiting hole is located at the opening of the first cover 04 and communicated fluidly to the opening. A part of the refrigeration component 02 is arranged in the limiting hole, and an edge of the refrigeration component 02 is 0.5-1 mm away from an edge of the limiting hole. A region of the heat sink 03 corresponding to the refrigeration component 02 defines a groove. The groove corresponds to the limiting hole. A part of the refrigeration component 02 is embedded in the groove and the other part of the refrigeration component 02 is located in the limiting hole. A ration of an area of the limiting hole to an area of the opening is between 0.8 and 1.2.

Specifically, the second cover 08 defines the limiting hole corresponding to the opening of the first cover 04 in the first direction. After the skin care assembly 1 is assembled, both the limiting hole and the opening of the first cover 04 are in the first direction and fluidly communicated to each other, such that the refrigeration component 02 may be thermally coupled to the cold compress component 01 to reduce the temperature of the cold compress component 01. In some embodiments, the groove corresponding to the refrigeration component 02 is defined in an end of the heat sink 03, and the part of the refrigeration component 02 is embedded in the groove. The refrigeration component 02 passes through the limiting hole of the second cover 08 and be connected to the cold-conducting layer 07, so as to reduce the temperature of the cold compress component 01.

In some embodiments, the skin care assembly described above further includes the heat-conducting housing 09 mounted on the second end of the heat sink 03 and configured to improve the heat-dissipating efficiency.

Specifically, a mounting column is arranged at the second end of the heat sink 03, and a third positioning hole is defined in the mounting column A fourth positioning hole is defined at an end of the heat-conducting housing. During mounting, after the third positioning hole is correspondingly attached to the fourth positioning hole, the heat-conducting housing is fixed to a side wall of the second end of the heat sink 03 through a screw. After mounted, a side wall of the heat-conducting housing is attached to the second end of the heat sink 03, such that the heat on the heat sink 03 may be efficiently conducted to the heat-conducting housing, thereby ensuring the heat-dissipating efficiency and an operating stability of the skin care assembly 1.

In some embodiments, the above skin care assembly 1 further includes the charging port 10 mounted on the pulse-generating circuit 05. The charging port 10 is located at a side where the second end of the heat sink 03 is located and configured to charge for the skin care assembly 1.

In some embodiments, the skin care assembly 1 may further include a skin color sensor and a skin detector, which are configured to realize a function of a skin color recognition. The skin detector and skin color sensor may quickly identify whether the beauty instrument is in direct contact with the skin and acquire a skin illuminance, and accurately control an output intensity of a beauty function such as the phototherapy, the radio frequency, the micro-current, or the like, according to acquired information by means of a control circuit and a dimming circuit. In this way, a problem that a skin contacted with the contacting surface feels uncomfortable or is damaged due to an improper intensity during use may be avoided, and a stability and adaptability to different skin tones of the beauty instrument may be permanently improved.

The above solutions and embodiments may be arbitrarily combined under a condition of no contradiction.

In some embodiments, the beauty instrument, the skin care assembly, etc. described in the embodiments of the present disclosure may not include the cold compress component, and only retain the refrigeration component, in this case, the refrigeration side of the refrigeration component may be directly contacted with the skin.

In some embodiments, in a case of omitting the cold compress component, the refrigeration side of the refrigeration component may be covered with some medium layers, such as an insulating layer.

In some embodiments, a mounting way of the refrigeration component 02 is that the refrigeration component 02 is pressed between the heat-dissipating body and the cold compress component by a certain pressure, and is limited by the limiting hole 24 of the second cover 08, such that a cost of processing the refrigeration component 02 and corresponding mounting structures may be saved. Even if the skin care assembly 1 falls off the ground or being collided in daily use, a structure of the skin care assembly 1 may still retain stable. The refrigeration component 02 will not be ejected out of the limiting hole 24 and stuck on the edge of the limiting hole 24 due to a deformation caused by a collision of such a degree. Therefore, the skin care component 1 may have better durability in the daily use.

The above is only some embodiments of the present disclosure and is not intended to limit the scope of the present disclosure. Any equivalent structure or equivalent process transformation using the specification and the accompanying drawings of the present disclosure, or direct or indirect application in other related technical fields, is included in the scope of the present disclosure.

What is claimed is:

1. A skin care assembly, comprising:
a first cover, defining a first opening;
an electrode, fixed on the first cover and configured to discharge for skin; and
a cold compress component, received in the first opening and configured to cool the skin;
a refrigeration component arranged on a side of the cold compress component away from the electrode and configured to cool the cold compress assembly; and
a heat sink, wherein the heat sink comprises a second cover and a heat-dissipating body connected with the second cover, the second cover is arranged between the first cover and the heat-dissipating body, the first cover and the second cover are fixed with each other, the second cover is defined with a limiting hole corresponding to and communicating with the first opening, and the refrigeration component is partially received in the limiting hole.

2. The skin care assembly according to claim 1, wherein the electrode is mounted on one side of the first cover, a first stepped surface is defined on an end of the cold compress component away from the electrode, a second stepped surface matched with the first stepped surface is defined on an end of a wall of the first opening away from the electrode, and the first stepped surface and the second stepped surface abut with each other.

3. The skin care assembly according to claim 2, wherein a first sealing component is arranged between the first stepped surface and the second stepped surface.

4. The skin care assembly according to claim 1, wherein the quantity of the electrode is multiple;
wherein the multiple electrodes are arranged at intervals around the cold compress component or at a side of the cold compress component, or the cold compress component is arranged around the multiple electrodes.

5. The skin care assembly according to claim 1, further comprising
a cold-conducting layer arranged between the cold compress component and the refrigeration component.

6. The skin care assembly according to claim 1, wherein an outer surface of the electrode is flush with or protruded from an outer surface of the cold compress component.

7. The skin care assembly according to claim 6, wherein both the outer surfaces of the electrode and the cold compress component are flush with or protruded from an out surface of the first cover.

8. The skin care assembly according to claim 1, wherein an end of the heat-dissipating body defines a contacting portion, the contacting portion is partially received in the limiting hole and contacted a side of the refrigeration component away from the cold compress component, and the other end of the heat-dissipating body extends in a direction away from the refrigeration component.

9. The skin care assembly according to claim 8, wherein an escape groove is defined in a side of the heat-dissipating body, a heat pipe is received in the escape groove, and the heat pipe is filled with liquid.

10. The skin care assembly according to claim 9, wherein an end of the heat pipe is bent and is abutted with an opposite surface of the contacting portion of the heat-dissipating body, and the other end of the heat pipe extends to a tail end of the heat-dissipating body.

11. The skin care assembly according to claim 9, wherein
the skin care assembly further comprises a mounting plate located at an opening side of the escape groove and extended to the tail end of the skin care assembly, and the mounting plate is provided with a circuit board; or
the skin care assembly further comprises a circuit board located at the opening side of the escape groove and extended to the tail end of the skin care assembly.

12. The skin care assembly according to claim 8, wherein a mounting ear is arranged on an end of the heat-dissipating body defining the contacting portion, the mounting ear is defined with a first mounting hole, a first mounting column is arranged on a side of the second cover facing the heat-dissipating body, a threaded hole is defined in the first mounting column, and the mounting ear is threadedly connected with the first mounting column.

13. The skin care assembly according to claim 1, wherein the first cover defines a first receiving cavity, the second cover is inserted in the first receiving cavity, and the cold compress component is arranged between the first cover and the second cover.

14. The skin care assembly according to claim 13, wherein the first cover comprises a first panel portion and a first side wall connected to the circumference of the first panel portion, the first panel portion and the first side wall cooperatively defines the first receiving cavity, a third mounting column is arranged in the first receiving cavity of the first cover, a threaded hole is defined in the third mounting column, the second cover comprises a second panel portion, the second cover defines a third mounting hole corresponding to the third mounting column, the first cover and the second cover are connected by threadedly connecting the third mounting column and the third mounting hole, and the cold compress component is arranged between the first cover and the second cover.

15. The skin care assembly according to claim 14, wherein the second cover further comprises a second side wall connected with the circumference of the second panel portion, the first side wall is abutted with the second side wall, and a second sealing component is arranged between the first side wall and the second side wall.

16. The skin care assembly according to claim 1, further comprising a phototherapy lamp board located on a side of the cold compress component opposite to the electrode, wherein a plurality of phototherapy lamps are arranged on the phototherapy lamp board, and the phototherapy lamps emit light to the outer side of the cold compress component.

17. The skin care assembly according to claim 16, further comprising a light-transmitting plate arranged between the first cover and the phototherapy lamp board, wherein a plurality of light-transmitting portions are defined on the light-transmitting plate corresponding to the plurality of phototherapy lamps, the electrode, the light-transmitting plate, and the phototherapy lamp board are connected with each other.

* * * * *